(12) United States Patent
Senn-Bilfinger et al.

(10) Patent No.: US 6,916,825 B2
(45) Date of Patent: Jul. 12, 2005

(54) ALKYLATED IMIDAZOPYRIDINE DERIVATIVES

(75) Inventors: Jörg Senn-Bilfinger, Constance (DE); Wilm Buhr, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/240,039

(22) PCT Filed: Mar. 28, 2001

(86) PCT No.: PCT/EP01/03507

§ 371 (c)(1), (2), (4) Date: Sep. 27, 2002

(87) PCT Pub. No.: WO01/72754

PCT Pub. Date: Oct. 4, 2001

(65) Prior Publication Data

US 2003/0158193 A1 Aug. 21, 2003

(30) Foreign Application Priority Data

Mar. 29, 2000 (EP) .............................. 00106696

(51) Int. Cl.⁷ .............................. A01N 43/42
(52) U.S. Cl. .................. 514/293; 514/233.2; 514/278; 544/126; 546/15; 546/82; 546/86
(58) Field of Search .............................. 546/82, 86, 15; 514/293, 233.2, 278; 544/126

(56) References Cited

U.S. PATENT DOCUMENTS 4,468,400 A   8/1984   Gold et al.

FOREIGN PATENT DOCUMENTS

| WO | 95/27714 | 10/1995 |
|---|---|---|
| WO | 98/42707 | 10/1998 |
| WO | 98/54188 | 12/1998 |

*Primary Examiner*—Bernard Dentz
(74) *Attorney, Agent, or Firm*—Nath & Associates PLLC; Joshua B. Goldberg; Sheldon M. McGee

(57) ABSTRACT

Compounds of the formula 1

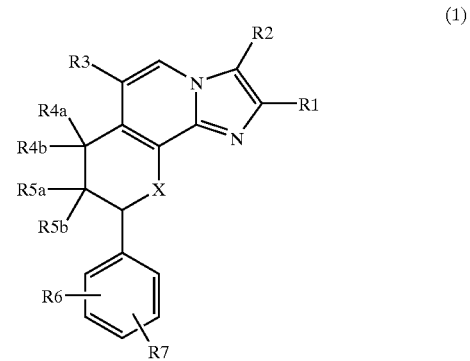

(1)

in which the substituents have the meanings mentioned in the description are suitable for the prevention and treatment of gastrointestinal diseases.

8 Claims, No Drawings

ALKYLATED IMIDAZOPYRIDINE DERIVATIVES

The application is a 371 of PCT/EP01/03507 filed Mar. 28, 2001.

FIELD OF APPLICATION OF THE INVENTION

The invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines with various ring systems fused to the imidazopyridine parent structure, which should be suitable for the treatment of peptic ulcers.—International Patent Application WO 95/27714 discloses certain substituted tricyclic imidazo[1,2-a]pyridines which are said to reversibly inhibit gastric acid secretion and to be useful in the prevention and treatment of gastrointestinal inflammatory diseases. International Patent Application WO 98/42707 discloses tetrahydroimidazo[1,2-h][1,7]naphthyridines which shall be suitable for the prevention and treatment of gastrointestinal diseases. WO 98/54188 describes fused dihydropyrans, which are said to be suitable for the treatment of peptic ulcer disorders.

DESCRIPTION OF THE INVENTION

The invention relates to compounds of the formula 1

(1)

in which

R1 is hydrogen, 1–4C-alkyl, 1–4C-alkoxy-1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3 is hydrogen, halogen, trifluoromethyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R4', or in which R4a and R4b together are O (oxygen) or 1–7C-alkylidene,
where R4' is a radical from which a hydroxyl group is formed under physiological conditions,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R5', or in which R5a and R5b together are O (oxygen) or 1–7C-alkylidene,
where R5' is a radical from which a hydroxyl group is formed under physiological conditions,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where at least one of the substituents R4a, R4b, R5a and R5b must have the meaning 1–7C-alkyl, 1–7C-alkenyl, phenyl or phen-1–4C-alkyl or where either R4a and R4b or R5a and R5b together must be 1–7C-alkylidene,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl,
R7 is hydrogen, halogen, 1–4C-alkyl or 1–4C-alkoxy and
X is O (oxygen) or NH,
where
R3a is hydrogen, 1–7C-alkyl, hydroxy-1–4C-alkyl or 1–4C-alkoxy-1–4C-alkyl and
R3b is hydrogen, 1–7C-alkyl, hydroxy-1–4C-alkyl or 1–4C-alkoxy-1–4C-alkyl,
or where
R3a and R3b together, including the nitrogen atom to which both are bonded, are a pyrrolidino, piperidino or morpholino radical,
and their salts.

1–4C-Alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical.

1–4C-Alkoxy represents radicals which, in addition to the oxygen atom, contain a straight-chain or branched alkyl radical having 1 to 4 carbon atoms, Examples which may be mentioned are the butoxy radical, isobutoxy radical, sec-butoxy radical, tert-butoxy radical, propoxy radical, isopropoxy radical and preferably the ethoxy radical and methoxy radical.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

Hydroxy-1–4C-alkyl represents abovementioned 1–4C-alkyl radicals which are substituted by a hydroxyl group. Examples which may be mentioned are the hydroxymethyl radical, the 2-hydroxyethyl radical and the 3-hydroxypropyl radical.

Halogen within the meaning of the invention is bromine, chlorine or fluorine.

2–4C-Alkenyl represents straight-chain or branched alkenyl radicals having 2 to 4 carbon atoms. Examples which may be mentioned are the 2-butenyl radical, 3-butenyl radical, 1-propenyl radical, the 2-propenyl radical (allyl radical) and the vinyl radical.

2–4C-Alkynyl represents straight-chain or branched alkynyl radicals having 2 to 4 carbon atoms. Examples which may be mentioned are the 2-butynyl radical, 3-butynyl radical and preferably the 2-propynyl radical (propargyl radical).

Fluoro-1–4C-alkoxy-1–4C-alkyl represents one of the abovementioned 1–4C-alkyl radicals which is substituted by a fluoro-1–4C-alkoxy radical. Fluoro-1–4C-alkoxy in this case represents one of the abovementioned 1–4C-alkoxy radicals which is completely or partly substituted by fluorine. Examples of 1–4C-alkoxy completely or partly substituted by fluorine which may be mentioned are the 1,1,1,3,3,3-hexafluoro-2-propoxy radical, the 2-trifluormethyl-2-propoxy radical, the 1,1,1-trifluoro-2-propoxy radical, the perfluoro-tert-butoxy radical, the 2,2,3,3,4,4,4-heptafluoro-1-butoxy radical, the 4,4,4-trifluoro-1-butoxy radical, the 2,2,3,3,3-pentafluoropropoxy radical, the perfluoroethoxy radical, the 1,2,2-trifluoroethoxy radical, in particular the 1,1,2,2-tetrafluoroethoxy radical, the 2,2,2-trifluoroethoxy radical, the trifluoromethoxy radical and preferably the difluoromethoxy radical.

1–7C-Alkyl represents straight-chain or branched alkyl radicals having 1 to 7 carbon atoms. Examples which may be mentioned are the heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

2–7C-Alkenyl represents straight-chain or branched alkenyl radicals having 2 to 7 carbon atoms. Examples which may be mentioned are the 2-butenyl radical, 3-butenyl radical, 1-propenyl radical, the 2-propenyl radical (allyl radical) and the vinyl radical. The abovementioned 2–4C-alkenyl radicals are preferred.

Phen-1–4C-alkyl represents one of the abovementioned 1–4C-alkyl radicals which is substituted by a phenyl radical. The phenethyl radical and in particular the benzyl radical are preferred.

1–4C-Alkoxy-1–4C-alkoxy represents one of the abovementioned 1–4C-alkoxy radicals which is substituted by a further 1–4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$—O—$CH_2$—$CH_2$—O—).

1–4C-Alkylcarbonyl represents a radical which, in addition to the carbonyl group, contains one of the abovementioned 1–4C-alkyl radicals. An example which may be mentioned is the acetyl radical.

1–4C-Alkylcarbonyloxy represents a 1–4C-alkylcarbonyl group which is bonded to an oxygen atom. An example which may be mentioned is the acetoxy radical ($CH_3CO$—O—).

1–7C-Alkylidene represents one of the abovementioned 1–7C-alkyl radicals, but bonded by a double bond. Examples which may be mentioned are the isopropylidene radical (($CH_3$)$_2$C=) and in particular the methylene radical ($H_2C$=).

A radical from which a hydroxyl group is formed under physiological conditions is understood as meaning a radical —OR', from which the group R' is removed hydrolytically in the human or animal body with formation of the radical —OH and the nontoxic compound R'OH. The radical R' can thus also be designated as a hydroxy protective group or as a "prodrug" radical. Such hydroxy protective groups or "prodrug" radicals are known, inter alia, from the patent applications and patents DE 4308095, WO 95/14016, EP 694547, WO 95/11884, WO 94/05282 and U.S. Pat. No. 5,432,183. For example, radicals R' having the general structure —C(O)R, —C(O)NRaRb, —P(O)ORaORb or —S(O)$_2$OR can be mentioned, where R, Ra and Rb are any desired organic radicals or optionally hydrogen. In one embodiment of the invention, R4' and R5' have a common hydroxy protective group R', which can then have, for example, one of the structures —CRaRb—, —CRa(ORb)—, —C(ORa)(ORb)— or —P(O)OR—.

1–4C-Alkylene represents straight-chain or branched 1–4C-alkylene radicals, for example the methylene radical (—$CH_2$—), ethylene radical (—$CH_2$—$CH_2$—), trimethylene radical (—$CH_2$—$CH_2$—$CH_2$—), tetramethylene radical (—$CH_2$—$CH_2$—$CH_2$—$CH_2$—), 1,2-dimethylethylene radical [—CH($CH_3$)—CH($CH_3$)—], 1,1-dimethylethylene radical [—C($CH_3$)$_2$—$CH_2$—], 2,2-dimethylethylene radical [—$CH_2$—C($CH_3$)$_2$—], isopropylidene radical [—C($CH_3$)$_2$—] and the 1-methylethylene radical [—CH($CH_3$)—$CH_2$—].

1–4C-Alkylenedioxy preferably represents the methylenedioxy radical (—O—$CH_2$—O—), the ethylenedioxy radical (—O—$CH_2$—$CH_2$—O—) or the isopropylidenedioxy radical (—O—C($CH_3$)$_2$—O—).

1–4C-Alkoxycarbonyl represents a carbonyl group to which one of the above-mentioned 1–4C-alkoxy radicals is bonded. Examples which may be mentioned are the methoxycarbonyl radical ($CH_3O$—C(O)—) and the ethoxycarbonyl radical ($CH_3CH_2O$—C(O)—).

1–4C-Alkoxycarbonylamino represents an amino radical which is substituted by one of the abovementioned 1–4C-alkoxycarbonyl radicals. Examples which may be mentioned are the ethoxycarbonylamino radical and the methoxycarbonylamino radical.

1–4C-Alkoxy-1–4C-alkoxycarbonyl represents a carbonyl group to which one of the abovementioned 1–4C-alkoxy-1–4C-alkoxy radicals is bonded. Examples which may be mentioned are the 2-(methoxy)ethoxycarbonyl radical ($CH_3$—O—$CH_2CH_2$—O—CO—) and the 2-(ethoxy)ethoxycarbonyl radical ($CH_3CH_2$—O—$CH_2CH_2$—O—CO—).

1–4C-Alkoxy-1–4C-alkoxycarbonylamino represents an amino radical which is substituted by one of the abovementioned 1–4C-alkoxy-1–4C-alkoxycarbonyl radicals. Examples which may be mentioned are the 2-(methoxy)ethoxycarbonylamino radical and the 2-(ethoxy)ethoxycarbonylamino radical.

Radicals R' to be mentioned in the context of the invention are the groups to be emphasized by way of example —C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—$C_6H_3$R1OR11,
—C(O)—OR8,
—C(O)-alk-C(O)—R8,
—C(O)-alk-C(O)—OR8,
—C(O)—C(O)—R8,
—C(O)—C(O)—OR8 and
—$CH_2$—OR8,
where
alk is 1–7C-alkylene,
R8 is hydrogen, 1–10C-alkyl or 1–4C-alkyl substituted by halogen, carboxyl, hydroxyl, sulfo (—$SO_3H$), sulfamoyl (—$SO_2NH_2$), carbamoyl (—$CONH_2$), 1–4C-alkoxy or 1–4C-alkoxycarbonyl,
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and R11 is hydrogen, halogen, 1–4C-alkyl or 1–4C-alkoxy.

1–7C-Alkylene represents straight-chain or branched 1–7C-alkylene radicals, for example the methylene radical (—CH$_2$—), ethylene radical (—CH$_2$CH$_2$—), trimethylene radical (—CH$_2$CH$_2$CH$_2$—), tetramethylene radical (—CH$_2$CH$_2$CH$_2$CH$_2$—), 1,2-dimethylethylene radical [—CH(CH$_3$)—CH(CH$_3$)], 1,1-dimethylethylene radical [—C(CH$_3$)$_2$—CH$_2$—], 2,2-dimethylethylene radical [—CH$_2$—C(CH$_3$)$_2$—], isopropylidene radical [—C(CH$_3$)$_2$—], 1-methylethylene radical [—CH(CH$_3$)—CH$_2$—], pentamethylene radical (—CH$_2$CH$_2$CH$_2$CH$_2$CH$_2$—), hexamethylene radical (—CH$_2$CH$_2$CH$_2$CH$_2$CH$_2$CH$_2$—) and the heptamethylene radical (—CH$_2$CH$_2$CH$_2$CH$_2$CH$_2$CH$_2$CH$_2$—).

1–10C-Alkyl within the meaning of the present invention represents straight-chain, branched or cyclic alkyl radicals having 1 to 10 carbon atoms. Examples which may be mentioned are the menthyl radical, neomenthyl radical, isomenthyl radical, neoisomenthyl radical, octyl radical, isooctyl radical (6-methylheptyl radical), heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

In this connection, radicals R' to be mentioned as particularly to be emphasized by way of example are the groups —C(O)—N(CH$_3$)$_2$, —C(O)—N(C$_2$H$_5$)$_2$, —C(O)—NHC$_2$H$_5$, —C(O)—CH$_2$CH$_2$NH$_2$, —C(O)—(CH$_2$)$_3$NH$_2$, —C(O)—C(CH$_3$)$_2$NH$_2$, —C(O)—CH$_2$N(CH$_3$)$_2$, —C(O)—CH(NH$_2$)—CH(CH$_3$)$_2$, —C(O)—CH(NH$_2$)CH(CH$_3$)C$_2$H$_5$, —C(O)—(CH$_2$)$_6$C(O)N(CH$_3$)CH$_2$CH$_2$SO$_3$H, —P(O)(OH)$_2$, —S(O)$_2$NH$_2$, —C(O)—H, —C(O)—C(CH$_3$)$_3$, —C(O)—CH$_2$CH$_2$COOH, —C(O)—CH$_3$, —C(O)—C$_2$H$_5$, —C(O)—C$_6$H$_5$, —C(O)—C$_6$H$_4$-4-NO$_2$, —C(O)—C$_6$H$_4$-3-NO$_2$, —C(O)—C$_6$H$_4$-4-OCH$_3$, —C(O)—C$_6$H$_4$-4-C(O)—OCH$_3$, —C(O)—OCH$_3$, —C(O)—O-menthyl, —C(O)—CH$_2$—C(O)—OCH$_3$, —C(O)—CH$_2$CH$_2$—C(O)—OCH$_3$, —C(O)—C(O)—OCH$_3$, —C(O)—C(O)—OC$_2$H$_5$ and —CH$_2$OCH(CH$_3$)$_2$, or (if R4' and R5' have a common hydroxy protective group) the groups —C(CH$_3$)$_2$—, —P(O)(OH)— and —CH[C(CH$_3$)$_3$]—.

Possible salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

It is known to the person skilled in the art that the compounds according to the invention and their salts, if they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

The compounds of the formula I have at least two chiral centers. The invention relates to all conceivable stereoisomers in any desired mixing ratio with one another, including the pure enantiomers, which are a preferred subject of the invention.

One embodiment (embodiment a) of the invention are compounds of the formula 1 in which R3 is hydrogen.

A further embodiment (embodiment b) of the invention are compounds of the formula 1 in which R3 is halogen.

A further embodiment (embodiment c) of the invention are compounds of the formula 1 in which R3 is carboxyl, —CO-1–4C-alkoxy or the radical —CO—NR3aR3b.

A further embodiment (embodiment d) of the invention are compounds of the formula 1 in which R3 is hydroxy-1–4C-alkyl, 1–4C-alkoxy-1–4C-alkyl or fluoro-1–4C-alkoxy-1–4C-alkyl.

A further embodiment (embodiment e) of the invention are compounds of the formula 1 in which R4a or R4b is not the radical R4' and at the same time R5a or R5b is not the radical R5'.

A preferred radical R1 by way of example is the methyl radical.

Preferred radicals R2 by way of example are the hydroxymethyl radical and in particular the methyl radical.

R3 in the context of the present invention is preferably hydrogen, halogen, carboxyl, —CO—-4C-alkoxy, hydroxy-1–4C-alkyl, 1–4C-alkoxy-1–4C-alkyl, fluoro-1–4C-alkoxy-1–4C-alkyl or the radical —CO—NR3aR3b.

Particularly worthy of mention in the context of the present invention are compounds of the formula 1, in which R1 is 1–4C-alkyl,
R2 is 1–4C-alkyl or hydroxy-1–4C-alkyl,
R3 is hydrogen, halogen, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO-NR3aR3b,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy or the radical —OR', or in which R4a and R4b together are O (oxygen) or 1–4C-alkylidene,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy or the radical —OR', or in which R5a and R5b together are O (oxygen) or 1–4C-alkylidene,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where at least one of the substituents R4a, R4b, R5a and R5b must have the meaning 1–7C-alkyl, 1–7C-alkenyl, phenyl or phen-1–4C-alkyl or where either R4a and R4b or R5a and R5b together must be 1–4C-alkylidene,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R7 is hydrogen, halogen, 1–4C-alkyl or 1–4C-alkoxy and
X is O (oxygen) or NH,
where
R3a is hydrogen, 1–7C-alkyl, hydroxy-1–4C-alkyl or 1–4C-alkoxy-1–4C-alkyl and
R3b is hydrogen, 1–7C-alkyl, hydroxy-1–4C-alkyl or 1–4C-alkoxy-1–4C-alkyl,
or where
R3a and R3b together, including the nitrogen atom to which both are bonded, are a pyrrolidino, piperidino or morpholino radical,
and where
R' is selected from the group consisting of
—C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—C$_6$H$_3$R10R11,
—C(O)—OR8,
—C(O)-alk-C(O)—R8,
—C(O)-alk-C(O)—OR8,
—C(O)—C(O)—R8,
—C(O)—C(O)—OR8 and
—CH$_2$—OR8,
where
alk is 1–7C-alkylene,
R8 is hydrogen, 1–10C-alkyl or 1–4C-alkyl substituted by halogen, carboxyl, hydroxyl, sulfo (—SO$_3$H), sulfamoyl (—SO$_2$NH$_2$), carbamoyl (—CONH$_2$), 1–4C-alkoxy or 1–4C-alkoxycarbonyl,
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and
R11 is hydrogen, halogen, 1–4C-alkyl or 1–4C-alkoxy, and the salts of the compounds.

Compounds of the invention to be emphasized are those of the formula 1*,

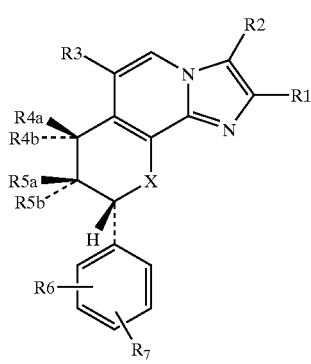

(1*)

in which

R1 is 1–4C-alkyl,
R2 is 1–4C-alkyl,
R3 is hydrogen, chlorine, fluorine, hydroxymethyl, difluoromethoxymethyl or the radical —CO—NR3aR3b,
one of the substituents R4a and R4b is hydrogen, 1–4C-alkyl, 2–4C-alkenyl, phenyl or benzyl and the other is hydroxyl, 1–4C-alkoxy, 1–4C-alkoxy-1–4C-alkoxy or the radical —OR', or in which R4a and R4b together are O (oxygen) or methylene,
one of the substituents R5a and R5b is hydrogen, 1–4C-alkyl, 2–4C-alkenyl, phenyl or benzyl and the other is hydroxyl, 1–4C-alkoxy, 1–4C-alkoxy-1–4C-alkoxy or the radical —OR', or in which R5a and R5b together are O (oxygen) or methylene,
or in which
one of the substituents R4a and R4b on the one hand and one of the substituents R5a and R5b on the other hand in each case is hydrogen, 1–4C-alkyl, 2–4C-alkenyl, phenyl or benzyl and the other substituents in each case together form a methylenedioxy, ethylenedioxy or isopropylidenedioxy radical,
where at least one of the substituents R4a, R4b, R5a and R5b must have the meaning 1–4C-alkyl, 2–4C-alkenyl, phenyl or benzyl or where either R4a and R4b or R5a and R5b together must be methylene,
R6 is hydrogen,
R7 is hydrogen and
X is O (oxygen) or NH,
where
R3a is hydrogen, 1–4C-alkyl, hydroxy-1–4C-alkyl or 1–4C-alkoxy-1–4C-alkyl and
R3b is hydrogen, 1–4C-alkyl, hydroxy-1–4C-alkyl or 1–4C-alkoxy-1–4C-alkyl,
and where
R' is selected from the group consisting of
—C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—C$_6$H$_3$R10R11,
—C(O)—OR8,
—C(O)-alk-C(O)—OR8,
—C(O)—C(O)—OR8 and
—CH$_2$—OR8,
where
alk is 1–7C-alkylene,
R8 is hydrogen, 1–10C-alkyl or 1–4C-alkyl substituted by carboxyl or sulfo (—SO$_3$H),
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and
R11 is hydrogen, halogen, 1–4C-alkyl or 1–4C-alkoxy, and the salts of the compounds.

Compounds of the formula 1* to be emphasized by way of example are those in which R' has the meaning —C(O)—N(CH$_3$)$_2$, —C(O)—N(C$_2$H$_5$)$_2$, —C(O)—NHC$_2$H$_5$, —C(O)—CH$_2$CH$_2$NH$_2$, —C(O)—(CH$_2$)$_3$NH$_2$, —C(O)—C(CH$_3$)$_2$NH$_2$, —C(O)—CH$_2$N(CH$_3$)$_2$, —C(O)—CH(NH$_2$)—CH(CH$_3$)$_2$, —C(O)—CH(NH$_2$)CH(CH$_3$)C$_2$H$_5$, —C(O)—(CH$_2$)$_6$C(O)N(CH$_3$)CH$_2$CH$_2$SO$_3$H, —P(O)(OH)$_2$, —S(O)$_2$NH$_2$, —C(O)—H, —C(O)—C(CH$_3$)$_3$, —C(O)—CH$_2$CH$_2$COOH, —C(O)—CH$_3$, —C(O)—C$_2$H$_5$, —C(O)—C$_6$H$_5$, —C(O)—C$_6$H$_4$-4-NO$_2$, —C(O)—C$_6$H$_4$-3-NO$_2$, —C(O)—C$_6$H$_4$-4-OCH$_3$, —C(O)—C$_6$H$_4$-4-C(O)—OCH$_3$, —C(O)—OCH$_3$, —C(O)—O-menthyl, —C(O)—CH$_2$—C(O)—OCH$_3$, —C(O)—CH$_2$CH$_2$—C(O)—OCH$_3$, —C(O)—C(O)—OCH$_3$, —C(O)—C(O)—OC$_2$H$_5$ or —CH$_2$OCH(CH$_3$)$_2$.

Compounds of the invention particularly to be emphasized are those of the formula 1*, in which R1 is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen, 1–4C-alkyl, 2–4C-alkenyl, phenyl or benzyl and the other is hydroxyl, 1–4C-alkoxy or 1–4C-alkoxy-1–4C-alkoxy, or in which R4a and R4b together are O (oxygen) or methylene,
one of the substituents R5a and R5b is hydrogen, 1–4C-alkyl, 2–4C-alkenyl, phenyl or benzyl and the other is hydroxyl,
or in which
one of the substituents R4a and R4b on the one hand and one of the substituents R5a and R5b on the other hand is in each case hydrogen, 1–4C-alkyl or 2–4C-alkenyl, and the other substituents in each case together are a methylenedioxy, ethylenedioxy or isopropylidenedioxy radical,
where at least one of the substituents R4a, R4b, R5a and R5b must have the meaning 1–4C-alkyl, 2–4C-alkenyl, phenyl or benzyl or where R4a and R4b together must be methylene,
R6 is hydrogen,
R7 is hydrogen and
X is O (oxygen) or NH,
where
R3a is hydrogen, methyl, ethyl, propyl, 2-hydroxyethyl or 2-methoxyethyl and
R3b is hydrogen, methyl or ethyl,
and the salts of the compounds.

Preferred compounds of the invention are those of the formula 1*, in which

R1 is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen, 1–4C-alkyl, 2–4C-alkenyl, phenyl or benzyl and the other is hydroxyl, 1–4C-alkoxy or 1–4C-alkoxy-1–4C-alkoxy, or in which R4a and R4b together are O (oxygen) or methylene,
R5a is 1–4C-alkyl, 2–4C-alkenyl, phenyl, benzyl or hydroxyl,
R5b is hydrogen or hydroxyl, where R5a and R5b are not simultaneously hydroxyl,
or in which
one of the substituents R4a and R4b on the one hand and one of the substituents R5a and R5b on the other hand is in each case hydrogen, 1–4C-alkyl or 2–4C-alkenyl, and the other substituents in each case together are a methylenedioxy, ethylenedioxy or isopropylidenedioxy radical,
where at least one of the substituents R4a, R4b, R5a and R5b must have the meaning 1–4C-alkyl, 2–4C-alkenyl, phenyl or benzyl or where R4a and R4b together must be methylene,
R6 is hydrogen,
R7 is hydrogen and
X is O (oxygen) or NH,
where
R3a is hydrogen, methyl, ethyl, propyl, 2-hydroxyethyl or 2-methoxyethyl and
R3b is hydrogen, methyl or ethyl,
and the salts of the compounds.

In the Examples below, the absolute configuration "R" for both positions 8 and 9 has been assigned to those compounds of formula 1* in which R5a is hydroxyl. The compounds of formula 1* in which R5b is hydroxy were described as compounds with "8S,9R" configuration in the Examples.

Preferred compounds of embodiment a of the invention are those of the formula 1* in which R3 is hydrogen.

Preferred compounds of embodiment b of the invention are those of the formula 1* in which R3 is chlorine or fluorine.

Preferred compounds of embodiment c of the invention are those of the formula 1* in which R3 is the radical —CO—NR3aR3b.

Preferred compounds of embodiment d of the invention are those of the formula 1* in which R3 is hydroxymethyl or difluoromethoxymethyl.

The following exemplary preferred compounds according to the invention may be mentioned in actual terms with the aid of the general formula 1*, in which R1 is methyl, R2 is methyl, R6 is hydrogen and R7 is hydrogen, by the substituent meanings for R3, R4a, R4b, R5a, R5b and X in the table 1 (tab. 1) below, where Ph is phenyl:

TABLE 1

| R3 | R4a | R4b | R5a | R5b | X |
|---|---|---|---|---|---|
| H | $CH_3$ | OH | OH | H | O |
| H | Ph | OH | OH | H | O |
| H | $PhCH_2$ | OH | OH | H | O |
| H | $CH_2=CH$ | OH | OH | H | O |
| H | $(CH_3)_2C=CH$ | OH | OH | H | O |
| H | $CH_3$ | OH | H | OH | O |
| H | Ph | OH | H | OH | O |
| H | $PhCH_2$ | OH | H | OH | O |
| H | $CH_2=CH$ | OH | H | OH | O |
| H | $(CH_3)_2C=CH$ | OH | H | OH | O |
| H | H | OH | $CH_3$ | OH | O |
| H | H | OH | Ph | OH | O |
| H | H | OH | $PhCH_2$ | OH | O |
| H | H | OH | $CH_2=CH$ | OH | O |
| H | H | OH | $(CH_3)_2C=CH$ | OH | O |
| H | OH | H | $CH_3$ | OH | O |
| H | OH | H | Ph | OH | O |
| H | OH | H | $PhCH_2$ | OH | O |

TABLE 1-continued

| R3 | R4a | R4b | R5a | R5b | X |
|---|---|---|---|---|---|
| H | OH | H | CH$_2$=CH | OH | O |
| H | OH | H | (CH$_3$)$_2$C=CH | OH | O |
| H | CH$_3$O | H | CH$_3$ | OH | O |
| H | CH$_3$O | H | Ph | OH | O |
| H | CH$_3$O | H | PhCH$_2$ | OH | O |
| H | CH$_3$O | H | CH$_2$=CH | OH | O |
| H | CH$_3$O | H | (CH$_3$)$_2$C=CH | OH | O |
| H | CH$_3$OCH$_2$CH$_2$O | H | CH$_3$ | OH | O |
| H | CH$_3$OCH$_2$CH$_2$O | H | Ph | OH | O |
| H | CH$_3$OCH$_2$CH$_2$O | H | PhCH$_2$ | OH | O |
| H | CH$_3$OCH$_2$CH$_2$O | H | CH$_2$=CH | OH | O |
| H | CH$_3$OCH$_2$CH$_2$O | H | (CH$_3$)$_2$C=CH | OH | O |
| F | CH$_3$ | OH | OH | H | O |
| F | Ph | OH | OH | H | O |
| F | PhCH$_2$ | OH | OH | H | O |
| F | CH$_2$=CH | OH | OH | H | O |
| F | (CH$_3$)$_2$C=CH | OH | OH | H | O |
| F | CH$_3$ | OH | H | OH | O |
| F | Ph | OH | H | OH | O |
| F | PhCH$_2$ | OH | H | OH | O |
| F | CH$_2$=CH | OH | H | OH | O |
| F | (CH$_3$)$_2$C=CH | OH | H | OH | O |
| F | H | OH | CH$_3$ | OH | O |
| F | H | OH | Ph | OH | O |
| F | H | OH | PhCH$_2$ | OH | O |
| F | H | OH | CH$_2$=CH | OH | O |
| F | H | OH | (CH$_3$)$_2$C=CH | OH | O |
| F | OH | H | CH$_3$ | OH | O |
| F | OH | H | Ph | OH | O |
| F | OH | H | PhCH$_2$ | OH | O |
| F | OH | H | CH$_2$=CH | OH | O |
| F | OH | H | (CH$_3$)$_2$C=CH | OH | O |
| F | CH$_3$O | H | CH$_3$ | OH | O |
| F | CH$_3$O | H | Ph | OH | O |
| F | CH$_3$O | H | PhCH$_2$ | OH | O |
| F | CH$_3$O | H | CH$_2$=CH | OH | O |
| F | CH$_3$O | H | (CH$_3$)$_2$C=CH | OH | O |
| F | CH$_3$OCH$_2$CH$_2$O | H | CH$_3$ | OH | O |
| F | CH$_3$OCH$_2$CH$_2$O | H | Ph | OH | O |
| F | CH$_3$OCH$_2$CH$_2$O | H | PhCH$_2$ | OH | O |
| F | CH$_3$OCH$_2$CH$_2$O | H | CH$_2$=CH | OH | O |
| F | CH$_3$OCH$_2$CH$_2$O | H | (CH$_3$)$_2$C=CH | OH | O |
| (CH$_3$OCH$_2$CH$_2$)NHCO | CH$_3$ | OH | OH | H | O |
| (CH$_3$OCH$_2$CH$_2$)NHCO | Ph | OH | OH | H | O |
| (CH$_3$OCH$_2$CH$_2$)NHCO | PhCH$_2$ | OH | OH | H | O |
| (CH$_3$OCH$_2$CH$_2$)NHCO | CH$_2$=CH | OH | OH | H | O |
| (CH$_3$OCH$_2$CH$_2$)NHCO | (CH$_3$)$_2$C=CH | OH | OH | H | O |
| (CH$_3$OCH$_2$CH$_2$)NHCO | CH$_3$ | OH | H | OH | O |
| (CH$_3$OCH$_2$CH$_2$)NHCO | Ph | OH | H | OH | O |
| (CH$_3$OCH$_2$CH$_2$)NHCO | PhCH$_2$ | OH | H | OH | O |
| (CH$_3$OCH$_2$CH$_2$)NHCO | CH$_2$=CH | OH | H | OH | O |
| (CH$_3$OCH$_2$CH$_2$)NHCO | (CH$_3$)$_2$C=CH | OH | H | OH | O |
| (CH$_3$OCH$_2$CH$_2$)NHCO | H | OH | CH$_3$ | OH | O |
| (CH$_3$OCH$_2$CH$_2$)NHCO | H | OH | Ph | OH | O |
| (CH$_3$OCH$_2$CH$_2$)NHCO | H | OH | PhCH$_2$ | OH | O |
| (CH$_3$OCH$_2$CH$_2$)NHCO | H | OH | CH$_2$=CH | OH | O |
| (CH$_3$OCH$_2$CH$_2$)NHCO | H | OH | (CH$_3$)$_2$C=CH | OH | O |
| (CH$_3$OCH$_2$CH$_2$)NHCO | OH | H | CH$_3$ | OH | O |
| (CH$_3$OCH$_2$CH$_2$)NHCO | OH | H | Ph | OH | O |
| (CH$_3$OCH$_2$CH$_2$)NHCO | OH | H | PhCH$_2$ | OH | O |
| (CH$_3$OCH$_2$CH$_2$)NHCO | OH | H | CH$_2$=CH | OH | O |
| (CH$_3$OCH$_2$CH$_2$)NHCO | OH | H | (CH$_3$)$_2$C=CH | OH | O |
| (CH$_3$OCH$_2$CH$_2$)NHCO | CH$_3$O | H | CH$_3$ | OH | O |
| (CH$_3$OCH$_2$CH$_2$)NHCO | CH$_3$O | H | Ph | OH | O |
| (CH$_3$OCH$_2$CH$_2$)NHCO | CH$_3$O | H | PhCH$_2$ | OH | O |
| (CH$_3$OCH$_2$CH$_2$)NHCO | CH$_3$O | H | CH$_2$=CH | OH | O |
| (CH$_3$OCH$_2$CH$_2$)NHCO | CH$_3$O | H | (CH$_3$)$_2$C=CH | OH | O |
| (CH$_3$OCH$_2$CH$_2$)NHCO | CH$_3$OCH$_2$CH$_2$O | H | CH$_3$ | OH | O |
| (CH$_3$OCH$_2$CH$_2$)NHCO | CH$_3$OCH$_2$CH$_2$O | H | Ph | OH | O |
| (CH$_3$OCH$_2$CH$_2$)NHCO | CH$_3$OCH$_2$CH$_2$O | H | PhCH$_2$ | OH | O |
| (CH$_3$OCH$_2$CH$_2$)NHCO | CH$_3$OCH$_2$CH$_2$O | H | CH$_2$=CH | OH | O |
| (CH$_3$OCH$_2$CH$_2$)NHCO | CH$_3$OCH$_2$CH$_2$O | H | (CH$_3$)$_2$C=CH | OH | O |
| HOCH$_2$ | CH$_3$ | OH | OH | H | O |
| HOCH$_2$ | Ph | OH | OH | H | O |
| HOCH$_2$ | PhCH$_2$ | OH | OH | H | O |
| HOCH$_2$ | CH$_2$=CH | OH | OH | H | O |
| HOCH$_2$ | (CH$_3$)$_2$C=CH | OH | OH | H | O |

TABLE 1-continued

| R3 | R4a | R4b | R5a | R5b | X |
|---|---|---|---|---|---|
| HOCH$_2$ | CH$_3$ | OH | H | OH | O |
| HOCH$_2$ | Ph | OH | H | OH | O |
| HOCH$_2$ | PhCH$_2$ | OH | H | OH | O |
| HOCH$_2$ | CH$_2$=CH | OH | H | OH | O |
| HOCH$_2$ | (CH$_3$)$_2$C=CH | OH | H | OH | O |
| HOCH$_2$ | H | OH | CH$_3$ | OH | O |
| HOCH$_2$ | H | OH | Ph | OH | O |
| HOCH$_2$ | H | OH | PhCH$_2$ | OH | O |
| HOCH$_2$ | H | OH | CH$_2$=CH | OH | O |
| HOCH$_2$ | H | OH | (CH$_3$)$_2$C=CH | OH | O |
| HOCH$_2$ | OH | H | CH$_3$ | OH | O |
| HOCH$_2$ | OH | H | Ph | OH | O |
| HOCH$_2$ | OH | H | PhCH$_2$ | OH | O |
| HOCH$_2$ | OH | H | CH$_2$=CH | OH | O |
| HOCH$_2$ | OH | H | (CH$_3$)$_2$C=CH | OH | O |
| HOCH$_2$ | CH$_3$O | H | CH$_3$ | OH | O |
| HOCH$_2$ | CH$_3$O | H | Ph | OH | O |
| HOCH$_2$ | CH$_3$O | H | PhCH$_2$ | OH | O |
| HOCH$_2$ | CH$_3$O | H | CH$_2$=CH | OH | O |
| HOCH$_2$ | CH$_3$O | H | (CH$_3$)$_2$C=CH | OH | O |
| HOCH$_2$ | CH$_3$OCH$_2$CH$_2$O | H | CH$_3$ | OH | O |
| HOCH$_2$ | CH$_3$OCH$_2$CH$_2$O | H | Ph | OH | O |
| HOCH$_2$ | CH$_3$OCH$_2$CH$_2$O | H | PhCH$_2$ | OH | O |
| HOCH$_2$ | CH$_3$OCH$_2$CH$_2$O | H | CH$_2$=CH | OH | O |
| HOCH$_2$ | CH$_3$OCH$_2$CH$_2$O | H | (CH$_3$)$_2$C=CH | OH | O |
| CHF$_2$OCH$_2$ | CH$_3$ | OH | OH | H | O |
| CHF$_2$OCH$_2$ | Ph | OH | OH | H | O |
| CHF$_2$OCH$_2$ | PhCH$_2$ | OH | OH | H | O |
| CHF$_2$OCH$_2$ | CH$_2$=CH | OH | OH | H | O |
| CHF$_2$OCH$_2$ | (CH$_3$)$_2$C=CH | OH | OH | H | O |
| CHF$_2$OCH$_2$ | CH$_3$ | OH | H | OH | O |
| CHF$_2$OCH$_2$ | Ph | OH | H | OH | O |
| CHF$_2$OCH$_2$ | PhCH$_2$ | OH | H | OH | O |
| CHF$_2$OCH$_2$ | CH$_2$=CH | OH | H | OH | O |
| CHF$_2$OCH$_2$ | (CH$_3$)$_2$C=CH | OH | H | OH | O |
| CHF$_2$OCH$_2$ | H | OH | CH$_3$ | OH | O |
| CHF$_2$OCH$_2$ | H | OH | Ph | OH | O |
| CHF$_2$OCH$_2$ | H | OH | PhCH$_2$ | OH | O |
| CHF$_2$OCH$_2$ | H | OH | CH$_2$=CH | OH | O |
| CHF$_2$OCH$_2$ | H | OH | (CH$_3$)$_2$C=CH | OH | O |
| CHF$_2$OCH$_2$ | OH | H | CH$_3$ | OH | O |
| CHF$_2$OCH$_2$ | OH | H | Ph | OH | O |
| CHF$_2$OCH$_2$ | OH | H | PhCH$_2$ | OH | O |
| CHF$_2$OCH$_2$ | OH | H | CH$_2$=CH | OH | O |
| CHF$_2$OCH$_2$ | OH | H | (CH$_3$)$_2$C=CH | OH | O |
| CHF$_2$OCH$_2$ | CH$_3$O | H | CH$_3$ | OH | O |
| CHF$_2$OCH$_2$ | CH$_3$O | H | Ph | OH | O |
| CHF$_2$OCH$_2$ | CH$_3$O | H | PhCH$_2$ | OH | O |
| CHF$_2$OCH$_2$ | CH$_3$O | H | CH$_2$=CH | OH | O |
| CHF$_2$OCH$_2$ | CH$_3$O | H | (CH$_3$)$_2$C=CH | OH | O |
| CHF$_2$OCH$_2$ | CH$_3$OCH$_2$CH$_2$O | H | CH$_3$ | OH | O |
| CHF$_2$OCH$_2$ | CH$_3$OCH$_2$CH$_2$O | H | Ph | OH | O |
| CHF$_2$OCH$_2$ | CH$_3$OCH$_2$CH$_2$O | H | PhCH$_2$ | OH | O |
| CHF$_2$OCH$_2$ | CH$_3$OCH$_2$CH$_2$O | H | CH$_2$=CH | OH | O |
| CHF$_2$OCH$_2$ | CH$_3$OCH$_2$CH$_2$O | H | (CH$_3$)$_2$C=CH | OH | O |
| H | CH$_3$ | OH | OH | H | NH |
| H | Ph | OH | OH | H | NH |
| H | PhCH$_2$ | OH | OH | H | NH |
| H | CH$_2$=CH | OH | OH | H | NH |
| H | (CH$_3$)$_2$C=CH | OH | OH | H | NH |
| H | CH$_3$ | OH | H | OH | NH |
| H | Ph | OH | H | OH | NH |
| H | PhCH$_2$ | OH | H | OH | NH |
| H | CH$_2$=CH | OH | H | OH | NH |
| H | (CH$_3$)$_2$C=CH | OH | H | OH | NH |
| H | H | OH | CH$_3$ | OH | NH |
| H | H | OH | Ph | OH | NH |
| H | H | OH | PhCH$_2$ | OH | NH |
| H | H | OH | CH$_2$=CH | OH | NH |
| H | H | OH | (CH$_3$)$_2$C=CH | OH | NH |
| H | OH | H | CH$_3$ | OH | NH |
| H | OH | H | Ph | OH | NH |
| H | OH | H | PhCH$_2$ | OH | NH |
| H | OH | H | CH$_2$=CH | OH | NH |
| H | OH | H | (CH$_3$)$_2$C=CH | OH | NH |
| H | CH$_3$O | H | CH$_3$ | OH | NH |
| H | CH$_3$O | H | Ph | OH | NH |

TABLE 1-continued

| R3 | R4a | R4b | R5a | R5b | X |
|---|---|---|---|---|---|
| H | CH$_3$O | H | PhCH$_2$ | OH | NH |
| H | CH$_3$O | H | CH$_2$=CH | OH | NH |
| H | CH$_3$O | H | (CH$_3$)$_2$C=CH | OH | NH |
| H | CH$_3$OCH$_2$CH$_2$O | H | CH$_3$ | OH | NH |
| H | CH$_3$OCH$_2$CH$_2$O | H | Ph | OH | NH |
| H | CH$_3$OCH$_2$CH$_2$O | H | PhCH$_2$ | OH | NH |
| H | CH$_3$OCH$_2$CH$_2$O | H | CH$_2$=CH | OH | NH |
| H | CH$_3$OCH$_2$CH$_2$O | H | (CH$_3$)$_2$C=CH | OH | NH |
| F | CH$_3$ | OH | OH | H | NH |
| F | Ph | OH | OH | H | NH |
| F | PhCH$_2$ | OH | OH | H | NH |
| F | CH$_2$=CH | OH | OH | H | NH |
| F | (CH$_3$)$_2$C=CH | OH | OH | H | NH |
| F | CH$_3$ | OH | H | OH | NH |
| F | Ph | OH | H | OH | NH |
| F | PhCH$_2$ | OH | H | OH | NH |
| F | CH$_2$=CH | OH | H | OH | NH |
| F | (CH$_3$)$_2$C=CH | OH | H | OH | NH |
| F | H | OH | CH$_3$ | OH | NH |
| F | H | OH | Ph | OH | NH |
| F | H | OH | PhCH$_2$ | OH | NH |
| F | H | OH | CH$_2$=CH | OH | NH |
| F | H | OH | (CH$_3$)$_2$C=CH | OH | NH |
| F | OH | H | CH$_3$ | OH | NH |
| F | OH | H | Ph | OH | NH |
| F | OH | H | PhCH$_2$ | OH | NH |
| F | OH | H | CH$_2$=CH | OH | NH |
| F | OH | H | (CH$_3$)$_2$C=CH | OH | NH |
| F | CH$_3$O | H | CH$_3$ | OH | NH |
| F | CH$_3$O | H | Ph | OH | NH |
| F | CH$_3$O | H | PhCH$_2$ | OH | NH |
| F | CH$_3$O | H | CH$_2$=CH | OH | NH |
| F | CH$_3$O | H | (CH$_3$)$_2$C=CH | OH | NH |
| F | CH$_3$OCH$_2$CH$_2$O | H | CH$_3$ | OH | NH |
| F | CH$_3$OCH$_2$CH$_2$O | H | Ph | OH | NH |
| F | CH$_3$OCH$_2$CH$_2$O | H | PhCH$_2$ | OH | NH |
| F | CH$_3$OCH$_2$CH$_2$O | H | CH$_2$=CH | OH | NH |
| F | CH$_3$OCH$_2$CH$_2$O | H | (CH$_3$)$_2$C=CH | OH | NH |
| (CH$_3$OCH$_2$CH$_2$)NHCO | CH$_3$ | OH | OH | H | NH |
| (CH$_3$OCH$_2$CH$_2$)NHCO | Ph | OH | OH | H | NH |
| (CH$_3$OCH$_2$CH$_2$)NHCO | PhCH$_2$ | OH | OH | H | NH |
| (CH$_3$OCH$_2$CH$_2$)NHCO | CH$_2$=CH | OH | OH | H | NH |
| (CH$_3$OCH$_2$CH$_2$)NHCO | (CH$_3$)$_2$C=CH | OH | OH | H | NH |
| (CH$_3$OCH$_2$CH$_2$)NHCO | CH$_3$ | OH | H | OH | NH |
| (CH$_3$OCH$_2$CH$_2$)NHCO | Ph | OH | H | OH | NH |
| (CH$_3$OCH$_2$CH$_2$)NHCO | PhCH$_2$ | OH | H | OH | NH |
| (CH$_3$OCH$_2$CH$_2$)NHCO | CH$_2$=CH | OH | H | OH | NH |
| (CH$_3$OCH$_2$CH$_2$)NHCO | (CH$_3$)$_2$C=CH | OH | H | OH | NH |
| (CH$_3$OCH$_2$CH$_2$)NHCO | H | OH | CH$_3$ | OH | NH |
| (CH$_3$OCH$_2$CH$_2$)NHCO | H | OH | Ph | OH | NH |
| (CH$_3$OCH$_2$CH$_2$)NHCO | H | OH | PhCH$_2$ | OH | NH |
| (CH$_3$OCH$_2$CH$_2$)NHCO | H | OH | CH$_2$=CH | OH | NH |
| (CH$_3$OCH$_2$CH$_2$)NHCO | H | OH | (CH$_3$)$_2$C=CH | OH | NH |
| (CH$_3$OCH$_2$CH$_2$)NHCO | OH | H | CH$_3$ | OH | NH |
| (CH$_3$OCH$_2$CH$_2$)NHCO | OH | H | Ph | OH | NH |
| (CH$_3$OCH$_2$CH$_2$)NHCO | OH | H | PhCH$_2$ | OH | NH |
| (CH$_3$OCH$_2$CH$_2$)NHCO | OH | H | CH$_2$=CH | OH | NH |
| (CH$_3$OCH$_2$CH$_2$)NHCO | OH | H | (CH$_3$)$_2$C=CH | OH | NH |
| (CH$_3$OCH$_2$CH$_2$)NHCO | CH$_3$O | H | CH$_3$ | OH | NH |
| (CH$_3$OCH$_2$CH$_2$)NHCO | CH$_3$O | H | Ph | OH | NH |
| (CH$_3$OCH$_2$CH$_2$)NHCO | CH$_3$O | H | PhCH$_2$ | OH | NH |
| (CH$_3$OCH$_2$CH$_2$)NHCO | CH$_3$O | H | CH$_2$=CH | OH | NH |

TABLE 1-continued

| R3 | R4a | R4b | R5a | R5b | X |
|---|---|---|---|---|---|
| $(CH_3OCH_2CH_2)NHCO$ | $CH_3O$ | H | $(CH_3)_2C=CH$ | OH | NH |
| $(CH_3OCH_2CH_2)NHCO$ | $CH_3OCH_2CH_2O$ | H | $CH_3$ | OH | NH |
| $(CH_3OCH_2CH_2)NHCO$ | $CH_3OCH_2CH_2O$ | H | Ph | OH | NH |
| $(CH_3OCH_2CH_2)NHCO$ | $CH_3OCH_2CH_2O$ | H | $PhCH_2$ | OH | NH |
| $(CH_3OCH_2CH_2)NHCO$ | $CH_3OCH_2CH_2O$ | H | $CH_2=CH$ | OH | NH |
| $(CH_3OCH_2CH_2)NHCO$ | $CH_3OCH_2CH_2O$ | H | $(CH_3)_2C=CH$ | OH | NH |
| $HOCH_2$ | $CH_3$ | OH | OH | H | NH |
| $HOCH_2$ | Ph | OH | OH | H | NH |
| $HOCH_2$ | $PhCH_2$ | OH | OH | H | NH |
| $HOCH_2$ | $CH_2=CH$ | OH | OH | H | NH |
| $HOCH_2$ | $(CH_3)_2C=CH$ | OH | OH | H | NH |
| $HOCH_2$ | $CH_3$ | OH | H | OH | NH |
| $HOCH_2$ | Ph | OH | H | OH | NH |
| $HOCH_2$ | $PhCH_2$ | OH | H | OH | NH |
| $HOCH_2$ | $CH_2=CH$ | OH | H | OH | NH |
| $HOCH_2$ | $(CH_3)_2C=CH$ | OH | H | OH | NH |
| $HOCH_2$ | H | OH | $CH_3$ | OH | NH |
| $HOCH_2$ | H | OH | Ph | OH | NH |
| $HOCH_2$ | H | OH | $PhCH_2$ | OH | NH |
| $HOCH_2$ | H | OH | $CH_2=CH$ | OH | NH |
| $HOCH_2$ | H | OH | $(CH_3)_2C=CH$ | OH | NH |
| $HOCH_2$ | OH | H | $CH_3$ | OH | NH |
| $HOCH_2$ | OH | H | Ph | OH | NH |
| $HOCH_2$ | OH | H | $PhCH_2$ | OH | NH |
| $HOCH_2$ | OH | H | $CH_2=CH$ | OH | NH |
| $HOCH_2$ | OH | H | $(CH_3)_2C=CH$ | OH | NH |
| $HOCH_2$ | $CH_3O$ | H | $CH_3$ | OH | NH |
| $HOCH_2$ | $CH_3O$ | H | Ph | OH | NH |
| $HOCH_2$ | $CH_3O$ | H | $PhCH_2$ | OH | NH |
| $HOCH_2$ | $CH_3O$ | H | $CH_2=CH$ | OH | NH |
| $HOCH_2$ | $CH_3O$ | H | $(CH_3)_2C=CH$ | OH | NH |
| $HOCH_2$ | $CH_3OCH_2CH_2O$ | H | $CH_3$ | OH | NH |
| $HOCH_2$ | $CH_3OCH_2CH_2O$ | H | Ph | OH | NH |
| $HOCH_2$ | $CH_3OCH_2CH_2O$ | H | $PhCH_2$ | OH | NH |
| $HOCH_2$ | $CH_3OCH_2CH_2O$ | H | $CH_2=CH$ | OH | NH |
| $HOCH_2$ | $CH_3OCH_2CH_2O$ | H | $(CH_3)_2C=CH$ | OH | NH |
| $CHF_2OCH_2$ | $CH_3$ | OH | OH | H | NH |
| $CHF_2OCH_2$ | Ph | OH | OH | H | NH |
| $CHF_2OCH_2$ | $PhCH_2$ | OH | OH | H | NH |
| $CHF_2OCH_2$ | $CH_2=CH$ | OH | OH | H | NH |
| $CHF_2OCH_2$ | $(CH_3)_2C=CH$ | OH | OH | H | NH |
| $CHF_2OCH_2$ | $CH_3$ | OH | H | OH | NH |
| $CHF_2OCH_2$ | Ph | OH | H | OH | NH |
| $CHF_2OCH_2$ | $PhCH_2$ | OH | H | OH | NH |
| $CHF_2OCH_2$ | $CH_2=CH$ | OH | H | OH | NH |
| $CHF_2OCH_2$ | $(CH_3)_2C=CH$ | OH | H | OH | NH |
| $CHF_2OCH_2$ | H | OH | $CH_3$ | OH | NH |
| $CHF_2OCH_2$ | H | OH | Ph | OH | NH |
| $CHF_2OCH_2$ | H | OH | $PhCH_2$ | OH | NH |
| $CHF_2OCH_2$ | H | OH | $CH_2=CH$ | OH | NH |
| $CHF_2OCH_2$ | H | OH | $(CH_3)_2C=CH$ | OH | NH |
| $CHF_2OCH_2$ | OH | H | $CH_3$ | OH | NH |
| $CHF_2OCH_2$ | OH | H | Ph | OH | NH |
| $CHF_2OCH_2$ | OH | H | $PhCH_2$ | OH | NH |
| $CHF_2OCH_2$ | OH | H | $CH_2=CH$ | OH | NH |
| $CHF_2OCH_2$ | OH | H | $(CH_3)_2C=CH$ | OH | NH |
| $CHF_2OCH_2$ | $CH_3O$ | H | $CH_3$ | OH | NH |
| $CHF_2OCH_2$ | $CH_3O$ | H | Ph | OH | NH |
| $CHF_2OCH_2$ | $CH_3O$ | H | $PhCH_2$ | OH | NH |
| $CHF_2OCH_2$ | $CH_3O$ | H | $CH_2=CH$ | OH | NH |
| $CHF_2OCH_2$ | $CH_3O$ | H | $(CH_3)_2C=CH$ | OH | NH |
| $CHF_2OCH_2$ | $CH_3OCH_2CH_2O$ | H | $CH_3$ | OH | NH |
| $CHF_2OCH_2$ | $CH_3OCH_2CH_2O$ | H | Ph | OH | NH |
| $CHF_2OCH_2$ | $CH_3OCH_2CH_2O$ | H | $PhCH_2$ | OH | NH |
| $CHF_2OCH_2$ | $CH_3OCH_2CH_2O$ | H | $CH_2=CH$ | OH | NH |
| $CHF_2OCH_2$ | $CH_3OCH_2CH_2O$ | H | $(CH_3)_2C=CH$ | OH | NH | and the salts of these compounds.

The compounds according to the invention can thus be prepared as described by way of example in the following examples, or using analogous process steps starting from corresponding starting compounds (see, for example, WO 98/42707, WO 98/54188, EP-A-299470 or Kaminski et al., J. Med. Chem. 1985, 28, 876–892 and Angew. Chem. 1996, 108, 589–591). The starting compounds are known or they can be prepared in an analogous manner to the known compounds. The compounds according to the invention can be prepared, for example, according to the following reaction schemes.

Scheme 1

In the following scheme, the preparation of the parent structure of the compounds of the formula 1 according to the invention where R1 = CH$_3$, R2 = CH$_3$, R4a or R4b and R5a or R5b = hydroxyl and X = O (oxygen) is outlined by way of example:

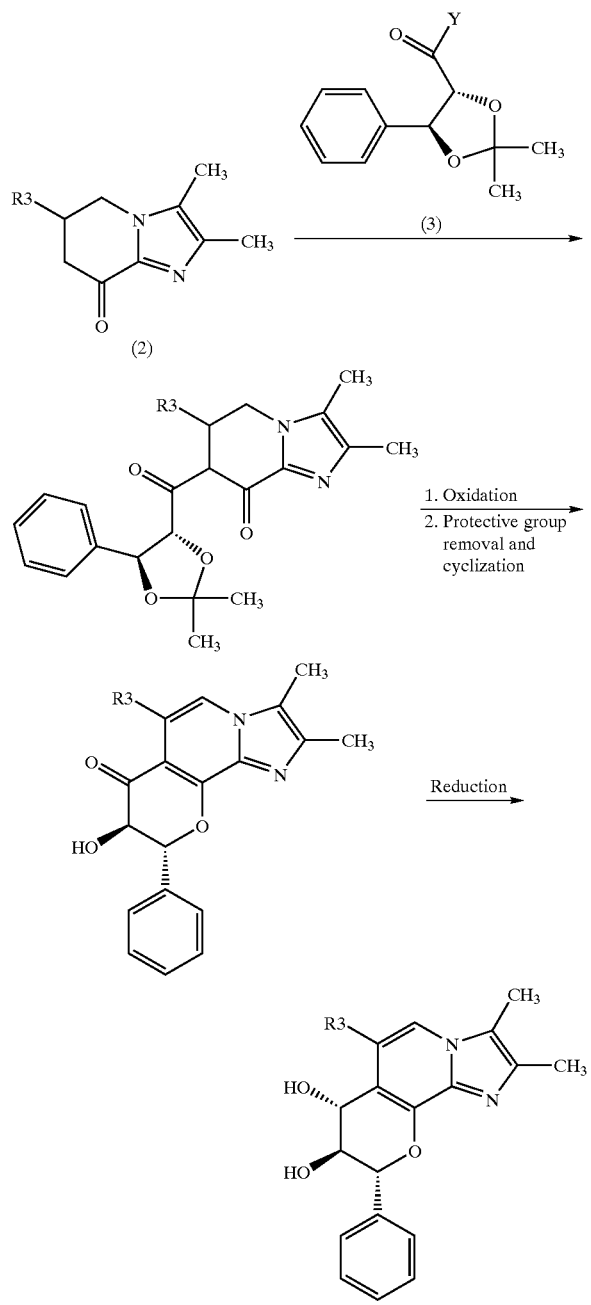

The above scheme 1 shows by way of example the enantioselective synthesis of a 7,8-diol (R4a or R4b and R5a or R5b are in each case hydroxyl) which can then be additionally alkylated and, if desired, additionally etherified in a suitable manner or provided with a prodrug radical.

The group Y in the above compound 3 is a suitable leaving group, for example a halogen atom, preferably chlorine. The acylation is carried out in a manner habitual to the person skilled in the art, preferably using bis (trimethylsilyl)sodium amide or -potassium amide if the leaving group is a chlorine atom.

The oxidation following the acylation is likewise carried out under conditions customary per se using chloranil, atmospheric oxygen or manganese dioxide as an oxidant. For the subsequent protective group removal and cyclization, certain conditions have to be fulfilled with respect to the auxiliary acid to be used. Advantageously, according to the invention formic acid is employed as an auxiliary acid.

The reduction to the diol is likewise carried out under standard conditions (see, for example, WO 98/54188), where, for example, sodium borohydride is employed as a reductant, on use of which the indicated 7,8-transdiol can be obtained in over 90% diastereomeric purity. The etherification which follows if desired, which is likewise carried out in a manner habitual per se, leads to the compounds of the formula 1* according to the invention in which R4a and R5b are hydrogen.

For the preparation of compounds of the formula 1 in which R5a and R5b are hydrogen, instead of compound 3, the starting materials to be used are 3-hydroxy-3-phenylpropionic acid derivatives (appropriately protected on the hydroxyl group) in which Y (analogously to the above scheme) is a suitable leaving group.

Scheme 2

In the scheme below, the preparation of the parent structure of the compounds of the formula 1 according to the invention where R1 = CH$_3$, R2 = CH$_3$, R4a or R4b = hydroxyl and X = NH starting from compounds of the formula 2 (see scheme 1) is outlined by way of example:

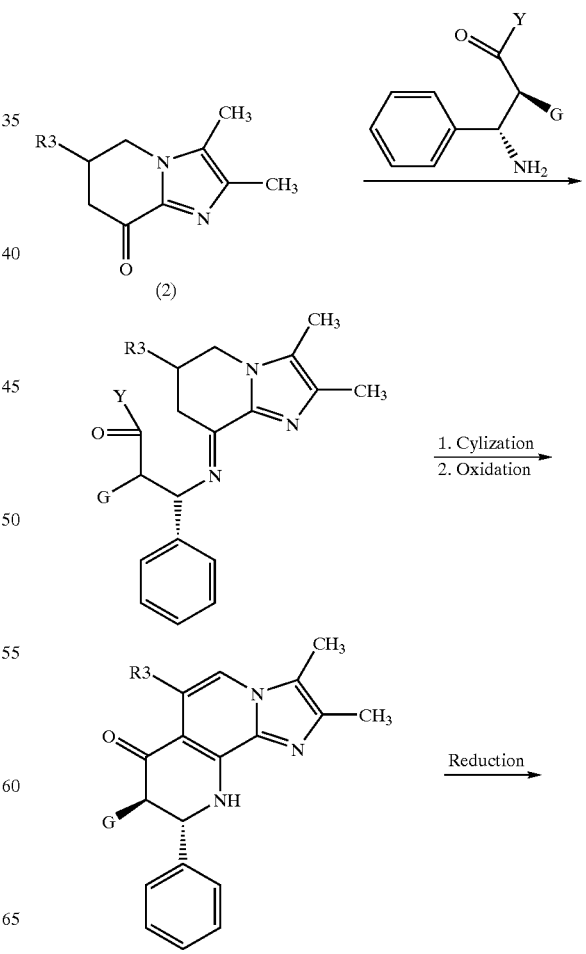

-continued

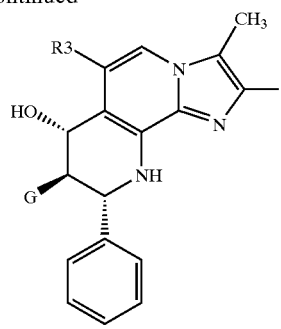

The above scheme 2 likewise, by way of example, is an enantioselective synthesis. Y is again a suitable leaving group, for example a methoxy group. The group G—depending on whether a compound where R5a and R5b=hydrogen or whether a compound where R5a or R5b= hydroxyl is desired—is either hydrogen or a hydroxyl group (for example protected by a suitable silyl radical).

The reduction of the keto group with sodium borohydride following the cyclization leads—in the case in which G is a hydroxyl group—in over 90% diastereomeric purity to the 7,8-trans diol. The etherification following if desired, which is carried out according to known processes, leads to the final products of the formula 1* in which R4a and R5b are hydrogen. The corresponding 7,8-cis compound is obtained by chromatographic purification from the mother liquor which remains after the separation of the 7,8-trans compound.

The introduction of the prodrug radical R' is carried out in the sense of an acylation reaction starting from compounds of the formula 1 in which at least one of the radicals R4a, R4b, R5a and R5b is a hydroxyl group, by reaction with compounds of the formula R'—Z, in which Z is a suitable leaving group, for example a halogen atom. The reaction is carried out in a manner known per se, e.g. as described in the examples, preferably in the presence of a suitable auxiliary base. For the preparation of the compounds of the formula 1 in which R4a or R4b is 1–4C-alkoxy or 1–4C-alkoxy-1–4C-alkoxy and R5a or R5b is the radical R5', compounds of the formula 1 in which R4a or R4b is 1–4C-alkoxy or 1–4C-alkoxy-1–4C-alkoxy and R5a or R5b is hydroxyl are reacted with compounds R'—Z. For the preparation of the compounds of the formula 1 in which R4a or R4b is hydroxyl and R5a or R5b is the radical R5', compounds of the formula 1 in which R4a and R4b together are O (oxygen) and R5a or R5b is hydroxyl are reacted with compounds R'—Z. The reduction of the keto group to the hydroxyl group is carried out subsequently. In a similar manner, compounds of the formula 1 are obtained in which the "prodrug" radical is in the 7-position and the hydroxyl or the 1–4C-alkoxy or 1–4C-alkoxy-1–4C-alkoxy radical is in the 8-position.

The alkylation of the compounds obtained according to schemes 1 and 2 to give the compounds of the formula 1 in which R4a, R4b, R5a or R5b have the meaning 1–7C-alkyl, 2–7C-alkenyl, phenyl or phen-1–4C-alkyl is carried out as described in the examples or generally according to schemes 3 and 4 below:

Scheme 3:

Scheme 3 generally outlines the preparation of compounds in which R4a or R4b has the meaning 1-7C-alkyl, 2-7C-alkenyl, phenyl or phen-1-4C-alkyl.

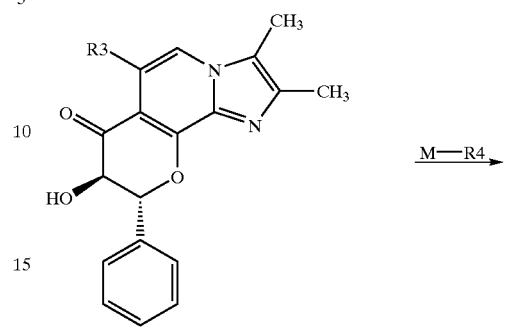

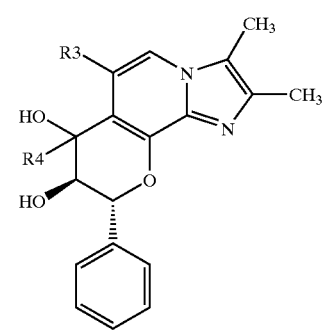

The introduction of the radical R4a or R4b (in brief designated as R4) in the 7-position takes place by reaction with a suitable organometallic (M=metal) compound (e.g. methyllithium phenyllithium, 2,2-dimethylvinylmagnesium bromide etc.) in a manner known per se. The 8-OH group is optionally to be protected, for example with a suitable silyl radical. Instead of the 7-oxo compound, the (optionally protected) 7-hydroxy compound can also be used as a starting compound. The alkylated product obtained can then, if desired, be reacted further as described or in a manner known per se (etherification, introduction of a prodrug radical etc.).

Scheme 4:

Scheme 4 generally outlines the preparation of compounds in which R5a or R5b has the meaning 1-7C-alkyl, 2-7C-alkenyl, phenyl or phen-1-4C-alkyl.

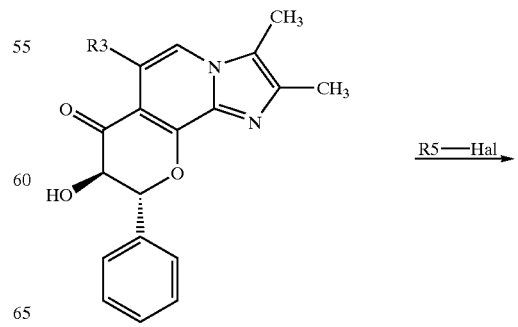

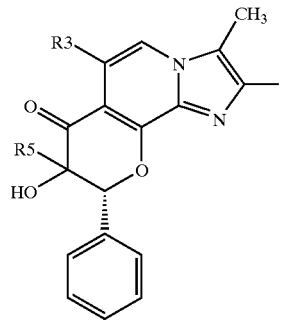

The introduction of the radical R5a or R5b (abbreviated by R5) in the 8-position takes place, for example, by reaction with a suitable halide (Hal=halogen), such as methyl iodide, benzyl bromide etc., under suitable, preferably basic conditions in a manner known per se. Advantageously, the reaction can also be carried out under phase-transfer conditions. The alkylated product obtained can then be reacted further, if desired, as described or in a manner known per se (reduction of the 7-oxo group, etherification, introduction of a prodrug radical etc.).

The isolation and purification of the substances according to the invention are carried out in a manner known per se, for example by distilling off the solvent in vacuo and recrystallizing the residue obtained from a suitable solvent or subjecting it to one of the customary purification methods, such as column chromatography on suitable support material.

Salts are obtained by dissolving the free compound in a suitable solvent, e.g. in a chlorinated hydrocarbon, such as methylene chloride or chloroform, or a low-molecular weight aliphatic alcohol (ethanol, isopropanol) which contains the desired acid, or to which the desired acid is then added. The salts are obtained by filtering, reprecipitating, precipitating with a nonsolvent for the addition salt or by evaporating the solvent. Salts obtained can be converted by alkalization or by acidification into the free compounds, from which salts can in turn be prepared. In this manner, pharmacologically nontolerable salts can be converted into pharmacologically tolerable salts.

The pure enantiomers, in particular the pure enantiomers of the formula 1*, which are a preferred subject of the invention, can be obtained in a manner familiar to the person skilled in the art, for example by enantioselective synthesis (see, for example, the scheme), by chromatographic separation on chiral separating columns, by derivatization with chiral auxiliary reagents, subsequent diastereomer separation and removal of the chiral auxiliary group, by salt formation with chiral acids, subsequent resolution of the salts and release of the desired compound from the salt, or by (fractional) crystallization from a suitable solvent. Trans products obtained (e.g. compounds 1* where R4a and R5b=hydrogen) can be converted—at least partly—into the corresponding cis products (e.g. where R4b and R5b=hydrogen) by allowing to stand under acidic conditions (e.g. in 2 equivalents of acid, such as sulfuric acid) in the corresponding alcohol R4a-OH. Likewise, cis products can be converted into the corresponding trans products. The cis and trans products are separated, for example, by chromatography or by crystallization.

The starting compounds of the formula 2 can be prepared starting from compounds known from the literature or with analogous use of processes known from the literature (e.g. Kaminski et al., J. Med. Chem. 1985, 28, 876–892), for example according to the general scheme 5 below:

Scheme 5

The scheme below outlines by way of example the preparation of a starting compound 2 where R3 = —COOC$_2$H$_5$.

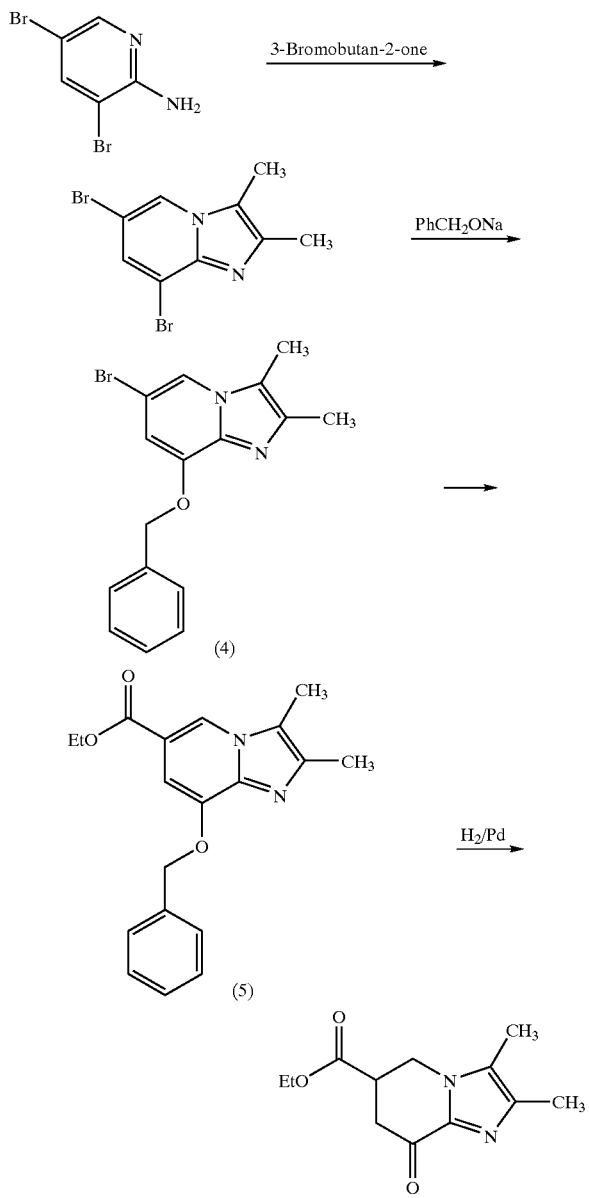

The reaction to give the compound 4 is carried out in a manner such as is known to the person skilled in the art. The reaction of 4 to 5 can be carried out in various ways, for example using the Heck reaction (with Pd(II), carbon monoxide and ethanol) or by metallation in the 6-position (with lithium or magnesium) and subsequent Grignard reaction. The metallation also offers the possibility of introducing other desired groups R3 in position 6, for example fluorine, chlorine or the carboxyl group. The debenzylation/reduction of the compound 5 is likewise carried out in a manner known per se, for example using hydrogen/Pd(0). If compounds where R3=—CO—NR5R6 are desired, an appropriate derivatization can be carried out in a manner known per se (conversion of an ester into an amide) at the stage of the compound 5 or after the debenzylation/reduction.

The following examples serve to illustrate the invention further without restricting it. Likewise, further compounds of the formula 1 whose preparation is not described explicitly can be prepared in an analogous manner or in a manner familiar per se to the person skilled in the art using customary process techniques. The abbreviation min stands for minute(s), h for hour(s) and ee for enantiomeric excess.

EXAMPLES

Final Products

1. (8S,9R)-2,3,8-Trimethyl-8-hydroxy-9-phenyl-7,8,9,10-tetrahydroimidazo[1,2-h][1,7]naphthyridin-7-one 20 g of (8R,9R)-2,3-dimethyl-8-hydroxy-9-phenyl-7,8,9,10-tetrahydroimidazo[1,2-h][1,7]naphthyridin-7-one (WO 98/42707) are dissolved in 100 ml of dichloromethane, and the solution is treated with 4 g of tetrabutylammonium hydrogensulfate, 70 ml of 50% strength aqueous sodium hydroxide solution and with 5 ml of methyl iodide, stirred vigorously at room temperature for 16 h, adjusted to pH 7 using ½ conc. hydrochloric acid with cooling and extracted three times with 100 ml of dichloromethane each time. The organic phases are combined, washed twice with a little water and concentrated to dryness on a rotary evaporator, and the residue obtained is purified twice on silica gel (1st eluent: dichloromethane/methanol 100/3; 2nd eluent: dichloromethane/methanol 100/1). 7.9 g of the title compound are obtained as a yellowish crystallizate of melting point 240° C.

2. (7R,8S,9R)-2,3,8-Trimethyl-7,8-dihydroxy-9-phenyl-7,8,9,10-tetrahydroimidazo[1,2-h][1,7]naphthyridine 8 g of (8S,9R)-2,3,8-trimethyl-8-hydroxy-9-phenyl-7,8,9,10-tetrahydroimidazo[1,2-h][1,7]naphthyridin-7-one are suspended in 160 ml of anhydrous methanol, and the suspension is treated with 2 g of sodium borohydride using a spatula and stirred at room temperature for 24 h, a solution being formed. It is then concentrated to dryness on a vacuum rotary evaporator, the residue is partitioned between water and dichloromethane (50 ml each), and the aqueous phase is adjusted to pH 8 using dilute hydrochloric acid and extracted twice with 200 ml of dichloromethane each time. The organic phases are combined, washed with a little water and dried over anhydrous sodium sulfate, the solvent is stripped off in vacuo and the residue obtained is washed with stirring in acetone. 5.3 g of the title compound are obtained as colorless crystals of melting point 180° C.

3. (8S,9R)-2,3-Dimethyl-8-benzyl-8-hydroxy-9-phenyl-7,8,9,10-tetrahydroimidazo[1,2-h][1,7]naphthyridin-7-one 2 g of (8S,9R)-2,3-dimethyl-8-hydroxy-9-phenyl-7,8,9,10-tetrahydroimidazo[1,2-h][1,7]naphthyridin-7-one, 1 g of Adogen 464, 7 ml of 50% strength aqueous sodium hydroxide solution and 0.8 ml of benzyl bromide are intensively stirred at room temperature for 16 h in 10 ml of dichloromethane. The mixture is then adjusted to pH 7 using ½ conc. aqueous hydrochloric acid with cooling and extracted three times with 100 ml of dichloromethane each time, and the organic phases are combined and washed twice with a little water. After stripping off the volatile components in vacuo, the residue obtained is chromatographed on silica gel (eluent: dichloromethane/methanol 100/3). 1.2 g of the title compound are obtained as yellowish crystals of melting point 248–51° C.

4. (7S,8S,9R)-2,3-Dimethyl-8-benzyl-7,8-dihydroxy-9-phenyl-7,8,9,10-tetrahydroimidazo[1,2-h][1,7]-naphthyridine A mixture of 0.8 g of (8S,9R)-2,3-dimethyl-8-benzyl-8-hydroxy-9-phenyl-7,8,9,10-tetrahydroimidazo-[1,2-h][1,7]naphthyridin-7-one suspended in 20 ml of methanol is treated in portions with 3.3 g of sodium borohydride (30 minutes), stirred at room temperature for 20 h and then refluxed for 5 h. It is then concentrated to dryness in vacuo and stirred into a mixture of 20 ml of water and 20 ml of dichloromethane, the mixture is adjusted to pH 8 using dilute hydrochloric acid with cooling, after separating off the aqueous phase this is extracted a further three times with 50 ml of dichloromethane each time, and the organic phases are combined, washed with a little water and concentrated to dryness in vacuo on a rotary evaporator. The residue obtained is purified on silica gel (eluent: dichloromethane/methanol 13/1). 0.3 g of the title compound of melting point 115–22° C. (diisopropyl ether) are obtained.

5. (7R,8S,9R)-2,3,8-Trimethyl-7,8,9,10-isopropylidene-9-phenyl-7,8,9,10-tetrahydroimidazo[1,2-h]-[1,7]naphthyridine 0.5 g of (7R,8S,9R)-2,3,8-trimethyl-7,8-dihydroxy-9-phenyl-7,8,9,10-tetrahydroimidazo[1,2-h][1,7]naphthyridine is suspended in 20 ml of 2,2-dimethoxypropane and treated with 2 g of p-toluenesulfonic acid, the mixture is stirred at room temperature for 18 h, the volatile components are stripped off in vacuo, the residue is treated with 100 ml of saturated aqueous sodium hydrogencarbonate solution and extracted three times with 50 ml of dichloromethane each time. The combined organic phases are concentrated to dryness in vacuo and the residue is chromatographed on silica gel (eluent: dichloromethane/methanol 13/1). 0.28 g of the title compound is obtained as yellowish crystals of melting point 236–7° C. (diethyl ether).

6. (7S,8S,9R)-2,3,8-Trimethyl-7-(2-methoxyethoxy)-8-hydroxy-9-phenyl-7,8,9,10-tetrahydroimidazo[1,2-h][1,7]naphthyridine A mixture of 0.5 g of (7R,8S,9R)-2,3,8-trimethyl-7,8-dihydroxy-9-phenyl-7,8,9,10-tetrahydroimidazo[1,2-h][1,7]naphthyridine and 0.2 ml of conc. sulfuric acid in 10 ml of 2-methoxyethanol is heated at an oil bath temperature of 60° C. for 24 h and then stirred at room temperature for 40 h. The reaction solution is poured into a mixture of 50 ml of saturated aqueous sodium hydrogencarbonate solution and 50 ml of dichloromethane and vigorously stirred. After separating off the organic phase, the aqueous phase is extracted a further three times with 50 ml of dichloromethane each time, the organic phases are combined, the solvent is stripped off in vacuo and the residue obtained is chromatographed on silica gel (eluent: diethyl ether/diethylamine 1/1). 0.3 g of the title compound is obtained as colorless crystals of melting point 1734° C. (diethyl ether).

7. (7S,8S,9R)-2,3,8-Trimethyl-7-methoxy-8-hydroxy-9-phenyl-7,8,9,10-tetrahydroimidazo[1,2-h]-[1,7]naphthyridine The title compound of melting point 190° C. (sintering) is obtained analogously to example 6 by treatment of (7R,8S,9R)-2,3,8-trimethyl-7,8-dihydroxy-9-phenyl-7,8,9,10-tetrahydroimidazo[1,2-h][1,7]naphthyridine with methanol.

8. (7R,8R,9R)-2,3,7-Trimethyl-7,8-dihydroxy-9-phenyl-7,8,9,10-tetrahydroimidazo[1,2-h][1,7]-naphthyridine 3.5 g of (8R,9R)-2,3-dimethyl-8-hydroxy-9-phenyl-7,8,9,10-tetrahydroimidazo[1,2-h][1,7]naphthyridin-7-one are suspended in 70 ml of tetrahydrofuran under argon and treated dropwise at −50° C. with a solution of methyllithium (1.6M solution in diethyl ether). The temperature is then allowed to rise to room temperature, and the mixture is poured into a saturated aqueous ammonium chloride solution and extracted three times with 100 ml of dichloromethane each time. The combined organic phases are washed with a little water, dried over sodium sulfate and concentrated to dryness in vacuo. The oily residue obtained is chromatographed on silica gel (eluent: dichloromethane/methanol 13/1). 1.66 g of the title compound are obtained as colorless crystals of melting point 137–8° C. (diethyl ether).

9. (7R,8R,9R)-2,3,7-Trimethyl-7,8-[1,3]dioxolo-9-phenyl-7,8,9,10-tetrahydroimidazo[1,2-h][1,7]-naphthyridine A mixture of 0.5 g of (7R,8S,9R)-2,3,7-trimethyl-7,8-dihydroxy-9-phenyl-7,8,9,10-tetrahydroimidazo[1,2-h][1,7]naphthyridine, 0.1 g of tetrabutylammonium bromide, 10 ml of 50% strength aqueous sodium hydroxide solution and 10 ml of dichloromethane is vigorously stirred at room temperature for 2 days. The mixture is adjusted to pH 8.7 using dilute hydrochloric acid with cooling and extracted three times with 50 ml of dichloromethane each time, the combined organic phases are washed with a little water, dried over anhydrous sodium sulfate and the solvent is stripped off in vacuo. The oily residue obtained is purified on silica gel (eluent: dichloromethane/methanol 100/3). 0.07 g of the title compound is obtained as pale yellow crystals of melting point 145–8° C. dec. (diethyl ether).

10. (8S,9R)-2,3-Dimethyl-8-hydroxy-7-methylidene-9-phenyl-7,8,9,10-tetrahydroimidazo[1,2-h][1,7]-naphthyridine A mixture of 1.0 g of (7R,8R,9R)-2,3,7-trimethyl-7,8-dihydroxy-9-phenyl-7,8,9,10-tetrahydroimidazo[1,2-h][1,7]naphthyridine and 0.45 g of conc. sulfuric acid in 15 ml of 2-methoxyethanol is vigorously stirred at room temperature for 48 h, the reaction mixture is poured into 50 ml of saturated aqueous sodium hydrogencarbonate solution, extracted three times with 50 ml of dichloromethane each time, and the organic phases are combined and washed with a little water. After stripping off the solvent in vacuo, the oily residue obtained is purified on silica gel (eluent: dichloromethane/methanol 100/1). 0.22 g of the title compound is obtained as pale yellow crystals of melting point 199–202° C. (diethyl ether).

11. (7S,8R,9R)-2,3,7-Trimethyl-7,8-dihydroxy-9-phenyl-7H-8,9-dihydropyrano[2,3-c]imidazo[1,2-a]-pyridine 2.40 ml (2.39 mmol/1M in THF) of methyllithium are slowly added dropwise to a solution of 0.40 g (1.19 mmol) of (7R,8R,9R)-2,3-dimethyl-7,8-dihydroxy-9-phenyl-7H-8,9-dihydropyrano[2,3-c]imidazo-[1,2-a]pyridine (WO 98/54188) in THF (10 ml) at −78° C. and the mixture is stirred at this temperature for a further 2 h. It is then slowly warmed to 0° C. The reaction is completed by addition of saturated NH$_4$Cl solution. The reaction mixture is extracted with dichloromethane. The combined organic phases are dried over Na$_2$SO$_4$ and concentrated in vacuo. The crude product is purified by column chromatography. The diastereoisomer mixture obtained is separated by HPLC. 80.0 mg (0.25 mmol/21%) of the title compound are thereby obtained as a pale brown solid having a melting point of >203° C.

12. (7R,8R,9R)-2,3,7-Trimethyl-7,8-dihydroxy-9-phenyl-7H-8,9-dihydropyrano[2,3-c]imidazo[1,2-a]-pyridine 2.40 ml (2.39 mmol/1M in THF) of methyllithium are slowly added dropwise to a solution of 0.40 g (1.19 mmol) of (7R,8R,9R)-2,3-dimethyl-7,8-dihydroxy-9-phenyl-7H-8,9-dihydropyrano[2,3-c]imidazo-[1,2-a]pyridine in THF (10 ml) at −78° C. and the mixture is stirred at this temperature for a further 2 h. It is then slowly warmed to 0° C. The reaction is completed by addition of saturated NH$_4$Cl solution. The reaction mixture is extracted with dichloromethane. The combined organic phases are dried over Na$_2$SO$_4$ and concentrated in vacuo. The crude product is purified by column chromatography. The diastereoisomer mixture obtained is separated by HPLC. 65.0 mg (0.20 mmol/17%) of the title compound are thereby obtained as a pale brown solid having a melting point of >205° C.

13. (7S,8R,9R)-2,3-Dimethyl-7,8-dihydroxy-7,9-diphenyl-7H-8,9-dihydropyrano[2,3-c]imidazo[1,2-a]-pyridine 11.90 ml (11.90 mmol/1M in THF) of phenyllithium are slowly added dropwise to a solution of 2.00 g (5.95 mmol) of (7R,8R,9R)-2,3-dimethyl-7,8-dihydroxy-9-phenyl-7H-8,9-dihydropyrano[2,3-c]imidazo-[1,2-a]pyridine in THF (10 ml) at −78° C. and the mixture is stirred at this temperature for a further 2 h. The reaction mixture is then slowly warmed to 25° C. and stirred for a further 8 h. The reaction is completed by addition of saturated NH$_4$Cl solution. The mixture is extracted with dichloromethane. The combined organic phases are dried over Na$_2$SO$_4$ and concentrated in vacuo. The crude product is purified by column chromatography. 1.66 g (4.29 mmol/72%) of the title compound are obtained as a colorless solid having a melting point of 281° C.

14. (7S,8R,9R)-2,3-Dimethyl-7-(2',2'-dimethylvinyl)-7,8-dihydroxy-9-phenyl-7H-8,9-dihydropyrano[2,3-c]imidazo[1,2-a]pyridine 23.80 ml (11.90 mmol/0.5M in THF) of 2,2-dimethylvinylmagnesium bromide are slowly added dropwise to a solution of 2.00 g (5.95 mmol) of (7R,8R,9R)-2,3-dimethyl-7,8-dihydroxy-9-phenyl-7H-8,9-dihydropyrano[2,3-c]imidazo[1,2-a]pyridine in THF (10 ml) at −78° C. and the mixture is stirred at this temperature for a further 2 h. It is then slowly warmed to 25° C. and stirred for a further 5 h. The reaction is completed by addition of saturated NH$_4$Cl solution. The mixture is extracted with dichloromethane. The combined organic phases are dried over Na$_2$SO$_4$ and concentrated in vacuo. The crude product is purified by column chromatography. 1.23 g (3.37 mmol/57%) of the title compound are obtained as a colorless solid.

$^1$H-NMR (200 MHz,[D6] DMSO): δ=1.64 (s, 3H), 1.72 (s, 3H), 2.22 (s, 3H), 2.34 (s, 3H), 3.91–4.08 (m, 1H), 4.99 (d, 1H), 5.51 (bs, 1H), 6.92 (d, 1H), 7.38–7.52 (m, 5H), 7.77 (d, 1H).

15. (7R,8R,9R)-2,3-Dimethyl-7,8-O-isopropylidene-9-phenyl-7-vinyl-7H-8,9-dihydropyrano[2,3-c]-imidazo[1,2-a]pyridine 0.40 g (3.03 mmol) of AlCl$_3$ dissolved in ether (5.0 ml) is added dropwise to a suspension of 0.34 g (1.01 mmol) of (7R,8R,9R)-2,3-dimethyl-7,8-dihydroxy-9-phenyl-7-vinyl-7H-8,9-dihydropyrano [2,3-c]-imidazo[1,2-a]pyridine in acetone (10 ml) and the mixture is stirred at 25° C. for 18 h. The reaction is completed by addition of saturated NaHCO$_3$ solution. The reaction mixture is extracted with EtOAc. The combined organic phases are washed with salt water, dried over Na$_2$SO$_4$ and concentrated in vacuo. The residue is separated and purified by column chromatography. 0.05 g (0.12 mmol/12%) of the title compound is obtained as a colorless solid having a melting point of 207° C.

Starting Compounds

A. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated to reflux for 9 days, and the precipitate formed is filtered off and dried in vacuo. It is then suspended in 1 l of water and the suspension is adjusted to pH 8 using 6 molar aqueous sodium hydroxide solution. The precipitate formed here is filtered off and washed with water. 28 g of the title compound of melting point over 90° C. (sintering) are obtained.

B. 8-Benzyloxy-6-bromo-2,3-dimethylimidazo[1,2-a]pyridine 34.8 ml of benzyl alcohol are added dropwise with ice-cooling to a suspension of 13.5 g of sodium hydride (60% strength suspension in paraffin) in 510 ml of dimethylformamide and the mixture is stirred for 1 h until the evolution of gas is complete. 51.2 g of 6,8-dibromo-2,3-dimethylimidazo[1,2-a]pyridine are then introduced in small portions and the mixture is stirred at room temperature for 40 h. It is then poured onto 1 l of ice water, extracted three times with 100 ml of dichloromethane each time, the combined organic extracts are washed with saturated aqueous ammonium chloride solution and twice with water and concentrated to dryness in vacuo, and the residue is stirred with a little ethyl acetate. The precipitate obtained here is filtered off and dried in vacuo. 43.2 g of the title compound of melting point 151–3° C. (ethyl acetate) are obtained.

C. 8-Benzyloxy-6-ethoxycarbonyl-2,3-dimethylimidazo[1,2-a]pyridine

A mixture of 4 g of 8-benzyloxy-6-bromo-2,3-dimethylimidazo[1,2-a]pyridine, 0.4 g of palladium(II) acetate, 1.33 g of triphenylphosphine, 10 ml of triethylamine and 50 ml of ethanol is heated for 16 h in a carbon monoxide atmosphere in an autoclave (5 bar), the volatile portions are stripped off in vacuo and the residue is chromatographed on silica gel (eluent: ethyl acetate). 2.4 g of the title compound of melting point 140–1° C. (diethyl ether) are obtained.

D. 6-Ethoxycarbonyl-2,3-dimethyl-5,6,7,8-tetrahydroimidazo[1,2-a]pyridine-8-one 3 g of 8-benzyloxy-6-ethoxycarbonyl-2,3-dimethylimidazo[1,2-a]pyridine, suspended in 50 ml of ethanol, are treated with 0.5 g of 10% strength palladium/active carbon and hydrogenated under a hydrogen pressure of 50 bar for 20 hours at an oil bath temperature of 75° C. After cooling, the catalyst is filtered off, the filtrate is concentrated to ⅕ of the volume in vacuo and the colorless precipitate formed here is filtered off. The filtrate from the precipitate is concentrated to dryness and chromatographed on silica gel (eluent: methylene chloride/methanol 100/3). 0.32 g of 6-ethoxycarbonyl-8-hydroxy-2,3-dimethyl-5,6,7,8-tetrahydroimidazo[1,2-a]pyridine is obtained. For conversion into the title compound, it is dissolved in chloroform, treated with 1.6 g of manganese dioxide and stirred at room temperature for 20 h. It is then filtered off, the filtrate is concentrated to dryness in vacuo and the residue obtained is purified on silica gel (eluent: methylene chloride/methanol 13/1). 0.2 g of the title compound of melting point 138–40° C. (diethyl ether) is obtained.

E. 8-Benzyloxy-6-hydroxymethyl-2,3-dimethylimidazo[1,2-a]pyridine

A solution of 1.2 g of 8-benzyloxy-6-ethoxycarbonyl-2,3-dimethylimidazo[1,2-a]pyridine in 20 ml of tetrahydrofuran is treated in small portions with 0.2 g of lithium aluminum hydride at room temperature, stirred for one hour and treated successively with 0.2 ml of water, 0.2 ml of 6 molar sodium hydroxide solution and 0.6 ml of water. It is then extracted twice with methylene chloride (50 ml each), the combined organic phases are concentrated to dryness in vacuo and the residue is purified on silica gel (eluent: methylene chloride/methanol 13/1). 0.4 g of the title compound of melting point 213–5° C. (acetone) is obtained.

F. 6-Hydroxymethyl-2,3-dimethyl-5,6,7,8-tetrahydroimidazo[1,2-a]pyridin-8-one Analogously to the process described in Example D, the title compound is obtained starting from 8-benzyloxy-6-hydroxymethyl-2,3-dimethylimidazo[1,2-a]pyridine by debenzylation/hydrogenation with palladium/active carbon.

G. 2,3-Dimethyl-6,7-dihydro-5H-imidazo[1,2-a]pyridin-8-one a) 500 g (2.35 mol) of 8-amino-2,3-dimethylimidazo[1,2-a]pyridine (see EP-A-299470) and 150 g of palladium on active carbon (10% Pd), suspended in 5.0 l of 6N hydrochloric acid, are stirred at 50° C. for 24 h under a hydrogen pressure of 10 bar. The catalyst is filtered off and the reaction mixture is concentrated to 2.0 l in vacuo. The solution obtained is extracted with dichloromethane. The aqueous phase is adjusted to pH 4.8–5.0 using concentrated ammonia solution and again extracted with dichloromethane. This procedure is repeated ten times. The combined organic phases are dried over sodium sulfate and concentrated. The crude product is crystallized from isopropanol. 334.1 g of the title compound are obtained in the form of pale brown crystals of melting point 178.5° C. (isopropanol).

Alternatively, the title compound can be prepared as follows:

b) A mixture of 252 g of 8-benzyloxy-2,3-dimethylimdazo[1,2-a]pyridine, 84 g of sodium hydrogencarbonate and 27 g of palladium/carbon catalyst (10% strength) in 500 ml of methanol is initially hydrogenated at 40° C. with hydrogen (5 bar) in an autoclave (20 h). The temperature is then reduced to 20° and the hydrogen pressure to 2 bar and hydrogenation is continued until the slow absorption of hydrogen is complete (about 10 h, TLC checking). The catalyst is then filtered off, the filter cake is washed with 200 ml of methanol, the filtrate is concentrated to dryness in vacuo, the residue is stirred with 200 ml of chloroform and insoluble material is filtered off. The filter cake is washed well with 150 ml of chloroform and the filtrate is concentrated to dryness in vacuo. 142 g of the title compound of melting point 178–9° C. (2-propanol) are obtained.

H. 2-Methyl-6,7-dihydro-5H-imidazo[1,2-a]pyridin-8-one

Analogously to the process described in Example Ga and starting from the compound 8-amino-2-methylimidazo[1,2-a]pyridine described in EP-A-299470, the title compound is obtained as a light brown solid of melting point 147–9° C. (dichloromethane).

I. 3-Formyl-2-methyl-6,7-dihydro-5H-imidazo[1,2-a]pyridin-8-one

Analogously to the process described in Example Ga, the title compound is obtained starting from the compound 8-amino-3-formyl-2-methylimidazo[1,2-a]pyridine described in EP-A-299470.

J. 6-Chloro-2-methyl-6,7-dihydro-5H-imidazo[1,2-a]pyridin-8-one

Analogously to the process described in Example D, the title compound is obtained starting from 8-benzyloxy-6-chloro-2-methylimidazo[1,2-a]pyridine (EP-A-299470) by debenzylation/hydrogenation with palladium/active carbon.

K. 6-Chloro-3-formyl-2-methyl-6,7-dihydro-5H-imidazo[1,2-a]pyridin-8-one

Analogously to the process described in Example D, the title compound is obtained starting from 8-benzyloxy-6-chloro-3-formyl-2-methylimidazo[1,2-a]pyridine (EP-A-299470) by debenzylation/hydrogenation with palladium/active carbon.

L. 6-Methoxymethyl-2,3-dimethyl-6,7-dihydro-5H-imidazo[1,2-a]pyridin-8-one

Analogously to the process described in Example D, the title compound of melting point 103-104° C. is obtained starting from 8-benzyloxy-6-methoxymethyl-2,3-dimethylimidazo[1,2-a]pyridine by debenzylation/hydrogenation with palladium/active carbon.

Commercial Applicability

The compounds of the formula 1 and their salts have valuable pharmacological properties which make them commercially utilizable. In particular, they exhibit pronounced inhibition of gastric acid secretion and an excellent gastric and intestinal protective action in warm-blooded animals, in particular humans. In this connection, the compounds according to the invention are distinguished by a high selectivity, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions, and of gastric acid-related diseases in mammals including man (such as, for example, gastric ulcers, duodenal ulcers, gastritis, hyperacidic or medicament-related functional gastropathy, reflux esophagitis, Zollinger-Ellison syndrome, heartburn), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations.

In their excellent properties, the compounds according to the invention surprisingly prove to be markedly superior to the compounds known from the prior art in various models in which the antiulcerogenic and the antisecretory properties are determined. On account of these properties, the compounds of the formula 1 and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention further relates to medicaments which contain one or more compounds of the formula 1 and/or their pharmacologically tolerable salts.

The medicaments are prepared by processes which are known per se and familiar to the person skilled in the art. As medicaments, the pharmacologically active compounds (=active compounds) according to the invention are either used as such, or preferably in combination with suitable pharmaceutical excipients or vehicles in the form of tablets, coated tablets, capsules, suppositories, patches (e.g. as TTS), emulsions, suspensions or solutions, the active compound content being advantageously between 0.1 and 95% and where a pharmaceutical administration form (e.g. a delayed-release form or an enteric form) exactly tailored to the active compound and/or to the desired onset of action and/or to the duration of action can be obtained by the appropriate choice of the excipients and vehicles.

The person skilled in the art knows, on the basis of his/her expert knowledge which excipients and vehicles are suitable for the desired pharmaceutical formulations. In addition to solvents, gel formers, suppository bases, tablet excipients and other active compound vehicles, it is possible to use, for example, antioxidants, dispersants, emulsifiers, antifoams, flavor corrigents, preservatives, solubilizers, colorants or in particular permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose from approximately 0.01 to approximately 20, preferably 0.05 to 5, in particular 0.1 to 1.5, mg/kg of body weight, if appropriate in the form of a number of, preferably 1 to 4, individual administrations to obtain the desired result. In the case of parenteral treatment, similar or (in particular in the case of intravenous administration of the active compounds), as a rule, lower doses can be used. Any person skilled in the art can easily determine on the basis of his/her expert knowledge the optimal dose and manner of administration of the active compound necessary in each case.

If the compounds according to the invention and/or their salts are to be employed for the treatment of the abovementioned diseases, the pharmaceutical preparations can also contain one or more pharmacologically active constituents of other pharmaceutical groups. The following examples may be mentioned: tranquillizers (for example from the benzodiazepines group, e.g. diazepam), spasmolytics (e.g. bietamiverine or camylofine), anticholinergics (e.g. oxyphencyclimine or phencarbamide), local anesthetics (e.g. tetracaine or procaine), and, if appropriate, also enzymes, vitamins or amino acids.

To be emphasized in particular in this connection is the combination of the compounds according to the invention with pharmaceuticals which inhibit acid secretion, such as $H_2$ blockers (e.g. cimetidine, ranitidine), $H^+/K^+$ ATPase inhibitors (e.g. omeprazole, pantoprazole), or furthermore with so-called peripheral anticholinergics (e.g. pirenzepine, telenzepine) and with gastric antagonists with the aim of potentiating the main action in the additive or superadditive sense and/or of eliminating or lowering the side effects, or furthermore the combination with antibacterially active substances (such as cephalosporins, tetracyclines, penicillins, macrolides, nitroimidazoles or alternatively bismuth salts) for the control of Helicobacter pylori. Examples of antibacterially active combination components which may be mentioned are mezlocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric acid secretion-inhibiting action of the compounds according to the invention can be demonstrated in investigations in animal experimental models. The compounds according to the invention investigated in the model mentioned below have been provided with numbers which correspond to the numbers of these compounds in the examples.

Testing of the Secretion-inhibiting Action on Perfused Rat Stomach

In table A below, the influence of the compounds according to the invention after intravenous administration is shown on the acid secretion of the perfused rat stomach stimulated by pentagastrin.

TABLE A

| No. | Dose (μmol/kg) i.v. | Inhibition of acid secretion (%) |
|---|---|---|
| 2 | 1 | 100 |
| 8 | 1 | 100 |
| 10 | 1 | 100 |
| 12 | 1 | 100 |

Methodology

The abdomen of anesthetized rats (CD rats, female, 200–250 g; 1.5 g/kg of i.m. urethane) was opened after tracheotomy by a median upper abdominal incision and a PVC catheter was fixed transorally in the esophagus and a further one via the pylorus such that the ends of the tubing just still projected into the gastric lumen. The catheter leading from the pylorus led outwards via a side opening in the right abdominal wall.

After thorough rinsing (about 50–100 ml), a continuous flow of warm physiological NaCl solution (0.5 ml/min, pH 6.8–6.9; Braun-Unita I) was continuously passed through the stomach at 37° C. The pH in the effluent, in each case collected at an interval of 15 minutes, was determined (pH meter 632, glass electrode EA 147; φ=5 mm, Metrohm) and the secreted HCl was determined by titration with a freshly prepared 0.01 N NaOH solution to pH 7 (Dosimat 665 Metrohm).

Gastric secretion was stimulated by continuous infusion of 1 μg/kg (=1.65 ml/h) of i.v. pentagastrin (left femoral vein) about 30 min after the end of the operation (i.e. after determination of 2 preliminary fractions). The substances to be tested were administered intravenously in 1 ml/kg of fluid volume 60 min after the start of the pentagastrin continuous infusion.

The body temperature of the animals was kept at a constant 37.8–38° C. by means of infrared irradiation and heating pads (automatic, step-free control via a rectal temperature sensor).

What is claimed is:
1. A compound of the formula 1

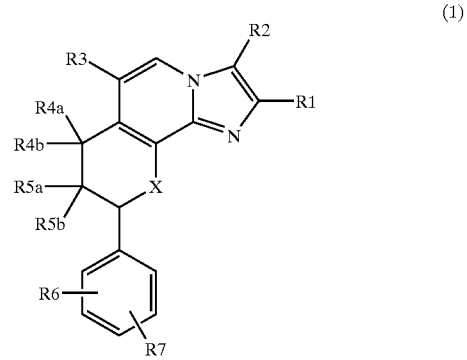

in which
R1 is hydrogen, 1–4C-alkyl, 1–4C-alkoxy-1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3 is hydrogen, halogen, trifluoromethyl, 1–4C-alkyl, 2–4C-alkenyl, 2–4-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R4', or in which R4a and R4b together are O (oxygen) or 1–7C-alkylidene,
where R4' is a radical from which a hydroxyl group is formed under physiological conditions,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R5', or in which R5a and R5b together are O (oxygen) or 1–7C-alkylidene,
where R5' is a radical from which a hydroxyl group is formed under physiological conditions,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where at least one of the substituents R4a, R4b, R5a and R5b must have the meaning 1–7C-alkyl, 1–7C-alkenyl, phenyl or phen-1–4C-alkyl or where either R4a and R4b or R5a and R5b together must be 1–7C-alkylidene,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl,
R7 is hydrogen, halogen, 1–4C-alkyl or 1–4C-alkoxy and
X is O (oxygen) or NH,
where
R3a is hydrogen, 1–7C-alkyl, hydroxy-1–4C-alkyl or 1–4C-alkoxy-1–4C-alkyl and
R3b is hydrogen, 1–7C-alkyl, hydroxy-1–4C-alkyl or 1–4C-alkoxy-1–4C-alkyl, or where R3a and R3b together, including the nitrogen atom to which both are bonded, are a pyrrolidino, piperidino or morpholino radical, or a solvate, hydrate, salt, hydrate of a salt or solvate of a salt thereof.

2. A compound of the formula 1 as claimed in claim 1, in which

R1 is 1–4C-alkyl,

R2 is 1–4C-alkyl or hydroxy-1–4C-alkyl,

R3 is hydrogen, halogen, carboxyl, —CO-1–4C-alkoxy, hydroxy-1–4C-alkyl, 1–4C-alkoxy-1–4C-alkyl, fluoro-1–4C-alkoxy-1–40-alkyl or the radical —CO—NR3aR3b, one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy or the radical —OR', or in which R4a and R4b together are O (oxygen) or 1–4C-alkylidene, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy or the radical —OR', or in which R5a and R5b together are O (oxygen) or 1–4C-alkylidene, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, where at least one of the substituents R4a, R4b, R5a and R5b must have the meaning 1–7C-alkyl, 1–7C-alkenyl, phenyl or phen-1–4C-alkyl or where either R4a and R4b or R5a and R5b together must be 1–4C-alkylidene, R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R7 is hydrogen, halogen, 1–4C-alkyl or 1–4C-alkoxy and X is O (oxygen) or NH, where R3a is hydrogen, 1–7C-alkyl, hydroxy-1–4C-alkyl or 1–4C-alkoxy-1–4C-alkyl and R3b is hydrogen, 1–7C-alkyl, hydroxy-1–4C-alkyl or 1–4C-alkoxy-1–4C-alkyl, or where R3a and R3b together, including the nitrogen atom to which both are bonded, are a pyrrolidino, piperidino or morpholino radical, and where R' is selected from the group consisting of

—C(O)—NR8R9,

—C(O)-alk-NR8R9,

—C(O)-alk-C(O)—NR8R9,

—P(O) (OH)$_2$,

—S(O)$_2$NR8R9,

—C(O)—R8,

—C(O)—C$_6$H$_3$R10R11,

—C(O)—OR8,

—C(O)-alk-C(O)—R8,

—C(O)-alk-C(O)—OR8,

—C(O)—C(O)—R8,

—C(O)—C(O)—OR8 and

—CH$_2$—OR8, where alk is 1–7C-alkylene,

R8 is hydrogen, 1–10C-alkyl or 1–4C-alkyl substituted by halogen, carboxyl, hydroxyl, sulfo(—SO$_3$H), sulfamoyl (—SO$_2$NH$_2$), carbamoyl (—CONH$_2$), 1–4C-alkoxy or 1–4C-alkoxycarbonyl, R9 is hydrogen or 1–4C-alkyl, R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and R11 is hydrogen, halogen, 1–4C-alkyl or 1–4C-alkoxy or a solvate, hydrate, salt, hydrate of a salt or solvate of a salt thereof.

3. A compound as claimed in claim 1, having the formula 1*

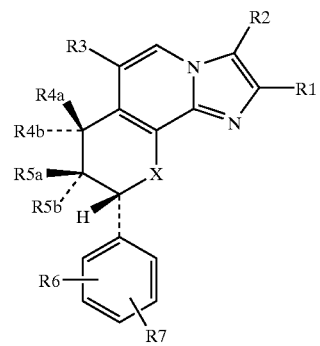

(1*)

in which

R1 is 1–4C-alkyl,

R2 is 1–4C-alkyl,

R3 is hydrogen, chlorine, fluorine, hydroxymethyl, difluoromethoxymethyl or the radical —CO—NR3aR3b, one of the substituents R4a and R4b is hydrogen, 1–4C-alkyl, 2–4C-alkenyl, phenyl or benzyl and the other is hydroxyl, 1–4C-alkoxy, 1–4C-alkoxy-1–4C-alkoxy, or the radical —OR', or in which R4a and R4b together are O (oxygen) or methylene, one of the substituents R5a and R5b is hydrogen, 1–4C-alkyl, 2–4C-alkenyl, phenyl or benzyl and the other is hydroxyl, 1–4C-alkoxy, 1–4C-alkoxy-1–4C-alkoxy, or the radical —OR', or in which R5a and R5b together are O (oxygen) or methylene, or in which one of the substituents R4a and R4b on the one hand and one of the substituents R5a and R5b on the other hand is in each case hydrogen, 1–4C-alkyl, 2–4C-alkenyl, phenyl or benzyl and the other substituents in each case together form a methylenedioxy, ethylenedioxy or isopropylidenedioxy radical, where at least one of the substituents R4a, R4b, R5a and R5b must have the meaning 1–4C-alkyl, 2–4C-alkenyl, phenyl or benzyl or where either R4a and R4b or R5a and R5b together must be methylene, R6 is hydrogen, R7 is hydrogen and X is O (oxygen) or NH,
where
R3a is hydrogen, 1–4C-alkyl, hydroxy-1–4C-alkyl or 1–4C-alkoxy-1–4C-alkyl and
R3b is hydrogen, 1–4C-alkyl, hydroxy-1–4C-alkyl or 1–4C-alkoxy-1–4C-alkyl,
and where
R' is selected from the group consisting of
—C(O)—NR8R9,
—C(O)-alk-NR8R9,
—C(O)-alk-C(O)—NR8R9,
—P(O) (OH)$_2$,
—S(O)$_2$NR8R9,
—C(O)—R8,
—C(O)—C$_6$H$_3$R10R11,
—C(O)—OR8,
—C(O)-alk-C(O)—R8,
—C(O)—C(O)—OR8 and
—CH$_2$—OR8,
where
alk is 1–7C-alkylene,
R8 is hydrogen, 1–10C-alkyl or 1–4C-alkyl substituted by carboxyl or sulfo(—SO$_3$H),
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-carbonylamino or trifluoromethyl and
R11 is hydrogen, halogen, 1–4C-alkyl or 1–4C-alkoxy,
or a solvate, hydrate, salt, hydrate of a salt or solvate of a salt thereof.

4. A compound as claimed in claim 1, which has the formula 1* in claim 3,
in which
R1 is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen, 1–4C-alkyl, 2–4C-alkenyl, phenyl or benzyl and the other is hydroxyl, 1–4C-alkoxy or 1–4C-alkoxy-1–4C-alkoxy, or in which R4a and R4b together are O (oxygen) or methylene,
one of the substituents R5a and R5b is hydrogen, 1–4C-alkyl, 2–4C-alkenyl, phenyl or benzyl and the other is hydroxyl,
or in which
one of the substituents R4a and R4b on the one hand and one of the substituents R5a and R5b on the other hand is in each case hydrogen, 1–4C-alkyl or 2–4C-alkenyl, and the other substituents in each case together are a methylenedioxy, ethylenedioxy or isopropylidenedioxy radical,
where at least one of the substituents R4a, R4b, R5a and R5b must have the meaning 1–4C-alkyl, 2–4C-alkenyl, phenyl or benzyl or where R4a and R4b together must be methylene,
R6 is hydrogen,
R7 is hydrogen and
X is O (oxygen) or NH,
where
R3a is hydrogen, methyl, ethyl, propyl, 2-hydroxyethyl or 2-methoxyethyl and
R3b is hydrogen, methyl or ethyl,
or a solvate, hydrate, salt, hydrate of a salt or solvate of a salt thereof.

5. A compound as claimed in claim 1, which has the formula 1* in claim 3,
in which
R1 is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen, 1–4C-alkyl, 2–4C-alkenyl, phenyl or benzyl and the other is hydroxyl, 1–4C-alkoxy or 1–4C-alkoxy-1–4C-alkoxy, or in which R4a and R4b together are O (oxygen) or methylene,
R5a is 1–4C-alkyl, 2–4C-alkenyl, phenyl, benzyl or hydroxyl,
R5b is hydrogen or hydroxyl, where R5a and R5b are not simultaneously hydroxyl,
or in which
one of the substituents R4a and R4b on the one hand and one of the substituents R5a and R5b on the other hand is in each case hydrogen, 1–4C-alkyl or 2–4C-alkenyl, and the other substituents in each case together are a methylenedioxy, ethylenedioxy or isopropylidenedioxy radical,
where at least one of the substituents R4a, R4b, R5a and R5b must have the meaning 1–4C-alkyl, 2–4C-alkenyl, phenyl or benzyl or where R4a and R4b together must be methylene,
R6 is hydrogen,
R7 is hydrogen and
X is O (oxygen) or NH,
where
R3a is hydrogen, methyl, ethyl, propyl, 2-hydroxyethyl or 2-methoxyethyl and
R3b is hydrogen, methyl or ethyl,
or a solvate, hydrate, salt, hydrate of a salt or solvate of a salt thereof.

6. A compound as claimed in claim 1, which has the formula 1* in claim 3,
in which
R1 is methyl,
R2 is methyl,
R3 is hydrogen,
one of the substituents R4a and R4b is hydrogen, 1–4C-alkyl, 2–4C-alkenyl, phenyl or benzyl and the other is hydroxyl, 1–4C-alkoxy or 1–4C-alkoxy-1–4C-alkoxy, or in which R4a and R4b together are O (oxygen) or methylene,
R5a is 1–4C-alkyl, 2–4C-alkenyl, phenyl, benzyl or hydroxyl,
R5b is hydrogen or hydroxyl, where R5a and R5b are not simultaneously hydroxyl,
or in which
one of the substituents R4a and R4b on the one hand and one of the substituents R5a and R5b on the other hand is in each case hydrogen, 1–4C-alkyl or 2–4C-alkenyl, and the other substituents in each case together are a methylenedioxy, ethylenedioxy or isopropylidenedioxy radical, where at least one of the substituents R4a, R4b, R5a and R5b must have the meaning 1–4C-alkyl, 2–4C-alkenyl, phenyl or benzyl or where R4a and R4b together must be methylene, R6 is hydrogen, R7 is hydrogen and X is O (oxygen) or NH, or a solvate, hydrate, salt, hydrate of a salt or solvate of a salt thereof.

7. A pharmaceutical composition comprising a compound as claimed in claim 1 and/or a pharmacologically tolerable solvate, hydrate, salt, hydrate of a salt or solvate of a salt thereof together with a suitable pharmaceutical excipient and/or vehicle.

8. A method of treating a gastrointestinal disease in a patient which comprises administering to a patient in need thereof a therapeutically effective amount of a compound as claimed in claim 1 or a pharmaceutically acceptable solvate, hydrate, salt, hydrate of a salt or solvate of a salt thereof.

* * * * *

UNITED STATES PATENT AND TRADEMARK OFFICE
CERTIFICATE OF CORRECTION

PATENT NO. : 6,916,825 B2
DATED : July 12, 2005
INVENTOR(S) : Senn-Bilfinger et al.

It is certified that error appears in the above-identified patent and that said Letters Patent is hereby corrected as shown below:

Column 35,
Lines 13-14, please delete "fluoro-1-4C-alkoxy-1-40-alkyl" and replace with -- fluoro-1-4C-alkoxy-1-4C-alkyl --.

Column 37,
Line 20, please delete "-C(O)-alk-C(O)-R8" and replace with -- -C(O)-alk-C(O)-OR8 --.

Signed and Sealed this

Sixth Day of September, 2005

JON W. DUDAS
*Director of the United States Patent and Trademark Office*